(12) United States Patent
Balman

(10) Patent No.: US 11,622,705 B2
(45) Date of Patent: Apr. 11, 2023

(54) APPARATUS AND METHOD FOR DETERMINING PHYSIOLOGICAL PARAMETERS OF AN INFANT IN-UTERO

(71) Applicant: James Robert Balman, Wichita, KS (US)

(72) Inventor: James Robert Balman, Wichita, KS (US)

( * ) Notice: Subject to any disclaimer, the term of this patent is extended or adjusted under 35 U.S.C. 154(b) by 0 days.

(21) Appl. No.: 17/555,256

(22) Filed: Dec. 17, 2021

(65) Prior Publication Data

US 2022/0110552 A1 Apr. 14, 2022

Related U.S. Application Data

(63) Continuation of application No. PCT/US2020/056050, filed on Oct. 16, 2020.

(Continued)

(51) Int. Cl.
*A61B 5/00* (2006.01)
*A61B 5/1482* (2006.01)
*A61B 5/145* (2006.01)

(52) U.S. Cl.
CPC ........ *A61B 5/1482* (2013.01); *A61B 5/14539* (2013.01); *A61B 5/14546* (2013.01);
(Continued)

(58) Field of Classification Search
CPC .............. A61B 5/1482; A61B 5/14539; A61B 5/14546; A61B 5/4356; A61B 5/4362;
(Continued)

(56) References Cited

U.S. PATENT DOCUMENTS 2,755,243 A 7/1956 Beckman et al.
3,098,813 A 7/1963 Beebe et al.
(Continued)

FOREIGN PATENT DOCUMENTS

AU 2019353533 B2 7/2021
CA 990364 A 6/1976
(Continued)

OTHER PUBLICATIONS

O'Brien Y. et al., "The reliability of foetal blood sampling as a test of foetal acidosis in labour", European Journal of Obstetrics & Gynecology and Reproductive Biology 167 (2013) 142-145.
(Continued)

*Primary Examiner* — May A Abouelela
(74) *Attorney, Agent, or Firm* — Fox Rothschild LLP

(57) ABSTRACT

In one aspect, an apparatus for monitoring a physiological condition of a patient is disclosed. The apparatus includes a body having an attachment portion configured to be inserted into the skin of a patient to affix the body to the patient. The apparatus includes a sensor coupled to the body that is configured to generate sensor data corresponding to a physiological condition of the patient when the body is secured to the skin of the patient. The apparatus further includes a reference sensor that is remote from the sensor coupled to the body and is configured to engage an outer surface of skin to generate reference data against which the sensor data is compared.

23 Claims, 16 Drawing Sheets

Related U.S. Application Data

(60) Provisional application No. 62/916,094, filed on Oct. 16, 2019.

(52) U.S. Cl.
CPC .......... *A61B 5/4356* (2013.01); *A61B 5/4362* (2013.01); *A61B 5/6882* (2013.01)

(58) Field of Classification Search
CPC . A61B 5/6882; A61B 5/02411; A61B 5/1455; A61B 5/1464
See application file for complete search history.

(56) References Cited

U.S. PATENT DOCUMENTS

| | | | |
|---|---|---|---|
| 3,145,157 A | 8/1964 | Arthur et al. | |
| 3,224,433 A | 12/1965 | Henry | |
| 3,224,436 A | 12/1965 | Le | |
| 3,415,731 A | 12/1968 | Carter | |
| 3,458,422 A | 7/1969 | Proctor, Jr. | |
| 3,476,670 A | 11/1969 | Weiner | |
| 3,659,586 A * | 5/1972 | Johns | A61B 5/14542 204/415 |
| 3,804,080 A | 4/1974 | Ruttgers et al. | |
| 3,827,428 A | 8/1974 | Hon et al. | |
| 3,961,623 A * | 6/1976 | Milani | A61N 1/0492 600/397 |
| 4,066,085 A | 1/1978 | Hess | |
| 4,105,509 A | 8/1978 | Jungck | |
| 4,144,890 A | 3/1979 | Hess | |
| 4,156,430 A | 5/1979 | King et al. | |
| 4,244,375 A | 1/1981 | Farrar et al. | |
| 4,252,124 A | 2/1981 | Maurer et al. | |
| 4,281,659 A * | 8/1981 | Farrar | A61B 5/1482 600/351 |
| 4,294,258 A | 10/1981 | Bernard | |
| 4,312,734 A | 1/1982 | Nichols | |
| 4,320,764 A | 3/1982 | Hon | |
| 4,378,813 A | 4/1983 | Lovelace et al. | |
| 4,384,927 A | 5/1983 | Nichols | |
| 4,549,553 A | 10/1985 | Hochberg | |
| 4,658,825 A * | 4/1987 | Hochberg | A61B 5/6882 600/386 |
| 4,913,151 A | 4/1990 | Harui et al. | |
| 4,989,615 A | 2/1991 | Hochberg | |
| 5,012,811 A * | 5/1991 | Malis | A61B 5/288 600/376 |
| 5,030,333 A * | 7/1991 | Clark, Jr. | A61B 5/14865 205/782 |
| 5,062,426 A | 11/1991 | Ulbrich et al. | |
| 5,184,619 A * | 2/1993 | Austin | A61B 5/344 600/561 |
| 5,188,803 A * | 2/1993 | Hochberg | A61B 5/14542 422/547 |
| 5,361,757 A * | 11/1994 | Smith | A61B 5/6848 600/476 |
| 5,388,579 A * | 2/1995 | Dowd | A61B 5/4362 600/376 |
| 5,404,876 A * | 4/1995 | DiSabito | A61B 5/4362 600/376 |
| 5,529,064 A * | 6/1996 | Rall | A61B 5/14542 600/382 |
| 5,551,424 A * | 9/1996 | Morrison | A61B 5/14542 600/338 |
| 5,671,736 A * | 9/1997 | Pettit | A61B 5/4362 600/376 |
| 5,776,058 A * | 7/1998 | Levinson | A61B 5/6885 600/338 |
| 5,865,737 A * | 2/1999 | Rall | A61B 5/14542 600/338 |
| 5,911,690 A * | 6/1999 | Rall | A61B 5/6848 600/338 |
| 5,928,144 A | 7/1999 | Real | |
| 6,058,321 A * | 5/2000 | Swayze | A61B 5/14539 600/310 |
| 6,115,624 A * | 9/2000 | Lewis | A61B 5/035 600/511 |
| 6,151,520 A * | 11/2000 | Combs | A61B 5/4362 439/669 |
| 6,285,896 B1 * | 9/2001 | Tobler | A61B 5/6882 600/323 |
| 6,292,679 B1 | 9/2001 | Sheard | |
| 6,363,271 B1 * | 3/2002 | Berry | A61F 13/42 600/304 |
| 6,567,679 B1 | 5/2003 | Khuri et al. | |
| 8,827,752 B2 * | 9/2014 | Gingsjo | H01R 9/03 439/669 |
| 9,737,226 B2 * | 8/2017 | Zhou | A61B 5/055 |
| 9,968,291 B2 * | 5/2018 | Hayes-Gill | A61B 5/4356 |
| 11,096,626 B2 * | 8/2021 | Recanati | A61B 5/0011 |
| 2003/0040665 A1 | 2/2003 | Khuri et al. | |
| 2004/0153008 A1 * | 8/2004 | Sharf | A61B 5/1127 600/588 |
| 2004/0193028 A1 | 9/2004 | Jones et al. | |
| 2005/0033130 A1 * | 2/2005 | Rall | A61B 5/1464 600/338 |
| 2005/0137486 A1 * | 6/2005 | Wallace | H01R 13/5224 600/511 |
| 2005/0283059 A1 | 12/2005 | Iyer et al. | |
| 2007/0299329 A1 * | 12/2007 | Pologe | A61B 5/14542 600/338 |
| 2008/0009749 A1 * | 1/2008 | Delianides | A61B 5/288 600/476 |
| 2008/0167553 A1 * | 7/2008 | Paltieli | A61B 5/1076 600/588 |
| 2008/0221420 A1 | 9/2008 | Grubac et al. | |
| 2008/0292597 A1 | 11/2008 | Steenblock | |
| 2011/0295097 A1 * | 12/2011 | Gingsjo | A61B 5/4362 600/376 |
| 2014/0073879 A1 * | 3/2014 | Cantor | A61B 5/435 600/304 |
| 2016/0249848 A1 * | 9/2016 | Blurton | A61B 5/4343 600/301 |
| 2016/0270658 A1 | 9/2016 | Ater | |
| 2017/0035347 A1 * | 2/2017 | Cantor | A61B 5/6875 |
| 2017/0215798 A1 * | 8/2017 | Lonky | A61M 25/01 |
| 2018/0344250 A1 * | 12/2018 | McKinney | A61M 31/005 |
| 2020/0029902 A1 * | 1/2020 | Kube | A61B 5/6832 |
| 2020/0268292 A1 * | 8/2020 | Morgan | A61B 5/14507 |
| 2021/0015375 A1 * | 1/2021 | Kim | A61B 5/4362 |
| 2021/0059538 A1 * | 3/2021 | Kumar | A61B 5/053 |
| 2021/0161633 A1 * | 6/2021 | Makin | A61C 19/04 |
| 2021/0315494 A1 * | 10/2021 | Challenor | A61B 5/6867 |

FOREIGN PATENT DOCUMENTS

| | | |
|---|---|---|
| DE | 2645048 A1 | 4/1977 |
| DE | 10151867 A1 | 5/2003 |
| HU | 48373 A | 7/1987 |
| WO | 2001-069227 A2 | 9/2001 |
| WO | 2004058322 A2 | 7/2004 |
| WO | 2004060479 A1 | 7/2004 |

OTHER PUBLICATIONS

Mahendru, A. et al., "Is intrapartum fetal blood sampling a gold standard diagnostic tool for fetal distress?", European Jounal of Obstetrics & Gynecology and Reproductive Biology, 156 (2011) 137-139. doi: 10.1016/j.ejogrb.2010.12.044. Epub Feb. 5, 2011. PMID: 21300427.

Einikyte, R. et al., "The comparison of umbilical cord arterial blood lactate and pH values for predicting short-term neonatal outcomes", Taiwan Jrl Obstet & Gynecol., 56(2017) pp. 745-749. doi: 10.1016/j.tjog.2017.10.007. PMID: 29241913.

Yagur, Y. et al., "Influencing parameters affecting fetal pH taken from category II tracing", American Journal of Obstetrics and Gynecology, Jan. 1, 2020. vol. 222, Issue 1, Supplement. pp. S501-S501.

(56) References Cited

OTHER PUBLICATIONS

Cantu, J. et al., "Predicting fetal acidemia using umbilical venous cord gas parameters", Obstet Gynecol., Nov. 2014, 124(5):926-932. doi: 10.1097/AOG.0000000000000517. PMID: 25437720.

Swanson, K. et al., "Can venous cord gas values predict fetal acidemia?", Am J Obstet Gynecol., Sep. 2017, 364.e1-364.e5. doi: 10.1016/j.ajog.2017.05.047. Epub May 31, 2017. PMID: 28578170.

Cohen, Y. et al., "Strong ion difference in fetal cord blood—A novel comprehensive approach to acid-base balance", American Journal of Obstetrics and Gynecology, Dec. 1, 2007, vol. 197, Issue 6, pp. S182-S182.

Lorenz, J. et al., "Fluid, Electrolyte, Acid-Base, and Renal-Developmental Physiology and Disorders", In Fetal and neonatal secrets. (2014). Chapter 9, 181-218.

Garite, T. et al., "The search for an adequate back-up test for intrapartum fetal heart rate monitoring", Am J Obstet Gynecol., Mar. 2013, pp. 163-164. doi: 10.1016/j.ajog.2012.12.001. Epub Dec. 13, 2012. PMID: 23246735.

Dildy III, G. et al., "Intrapartum assessment of the fetus: historical and evidence-based practice", Obstet Gynecol Clin North Am. 32 (2005) 255-271, ix. doi: 10.1016/j.ogc.2005.01.005. PMID: 15899359.

McNamara, H. et al., "Continuous intrapartum pH, pO2, pCO2, and SpO2 monitoring", Obstet Gynecol Clin North Am., Dec. 1999, 26(4):671-93. doi: 10.1016/s0889-8545(05)70106-6. PMID: 10587962.

Flynn, A. et al., "The continuous measurement of tissue ph in the human fetus during labour using a new application technique", British Journal of Obstetrics and Gynaecology, Aug. 1980, vol. 87, pp. 666-668; https://doi.org/10.1097/00006254-198106000-00004.

Bowen, L. et al., "Maternal-fetal pH difference and fetal scalp pH as predictors of neonatal outcome", Obstet Gynecol., vol. 67, No. 4, pp. 487-495, Apr. 1986. PMID: 3960419.

Nickelsen, C. et al. "Evaluation of a needle pH electrode for continuous tissue-pH monitoring during labor. Characteristics during acidosis in the rat.", Int J Gynaecol. Obstet. 1986, 24: 459-466; doi: 10.1016/0020-7292(86) 90039-1; PMID: 20419911.

Nickelsen, C. et al., "Continuous acid-base assessment of the human fetus during labour by tissue pH and transcutaneous carbon dioxide monitoring", Br J Obstet Gynaecol., Mar. 1985, vol. 92, pp. 220-225. doi: 10.1111/j.1471-0528.1985.tb01086.x. PMID: 3919756.

P.J. Steer "Technical Aspects of Fetal and Intrauterine Pressure Monitoring", Editor(s): Richard W. Beard, Peter W. Nathanielsz, Fetal Physiology and Medicine (Second Edition), Butterworth-Heinemann, 1984, pp. 679-711.

Chatterjee M. et al., "Fetal tissue pH-continuous intrapartum monitoring", Int J Gynaecol Obstet., 1948, 22: 41-46. doi: 10.1016/0020-7292(84)90102-4. PMID: 6144590.

C. Antoine et al., "Current status of continuous fetal pH monitoring", Clin Perinatol. Jun. 1982; 9(2): 409-422. PMID: 6749380.

Fusi, L. et al. "An Evaluation of the tissue pH electrode for fetal monitoring using the fetal sheep as an experimental model", Am J Obstet Gynecol., Aug. 15, 1981, 140(8):953-60. doi: 10.1016/0002-9378(81)90091-0. PMID: 7270608.

Wood, C. et al., "Continuous measurement of tissue pH in the human fetal scalp", Br J Obstet Gynaecol. vol. 85, pp. 668-677, Sep. 1978. doi: 10.1111/j.1471-0528.1978.tb14945.x. PMID: 29656.

Huch, A. et al., "Continuous transcutaneous monitoring of fetal oxygen tension during labour" Br J Obstet Gynaecol. 1977; 84 Suppl 1:1-39. doi: 10.1111/j.1471-0528.1977.tb16231.x. PMID: 588510 (39 pages).

* cited by examiner

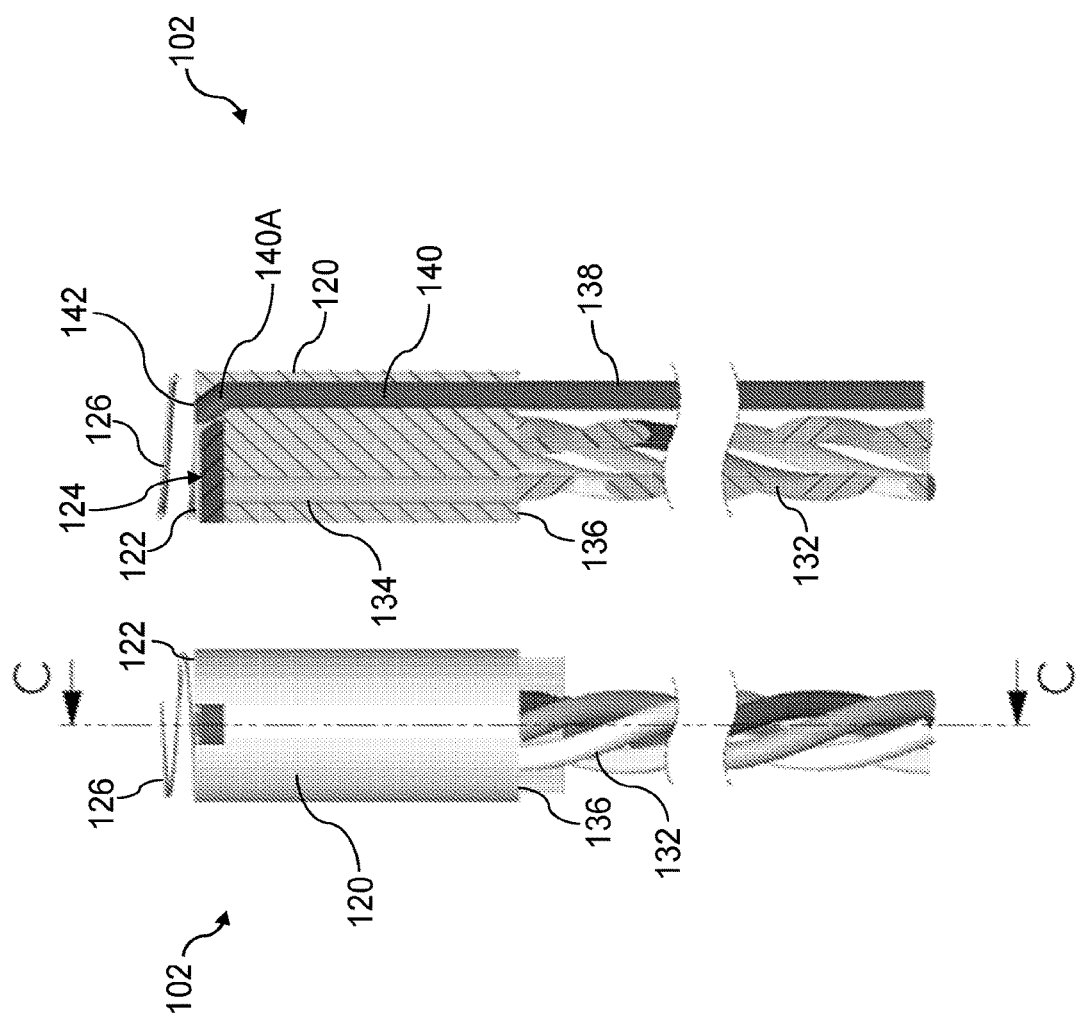

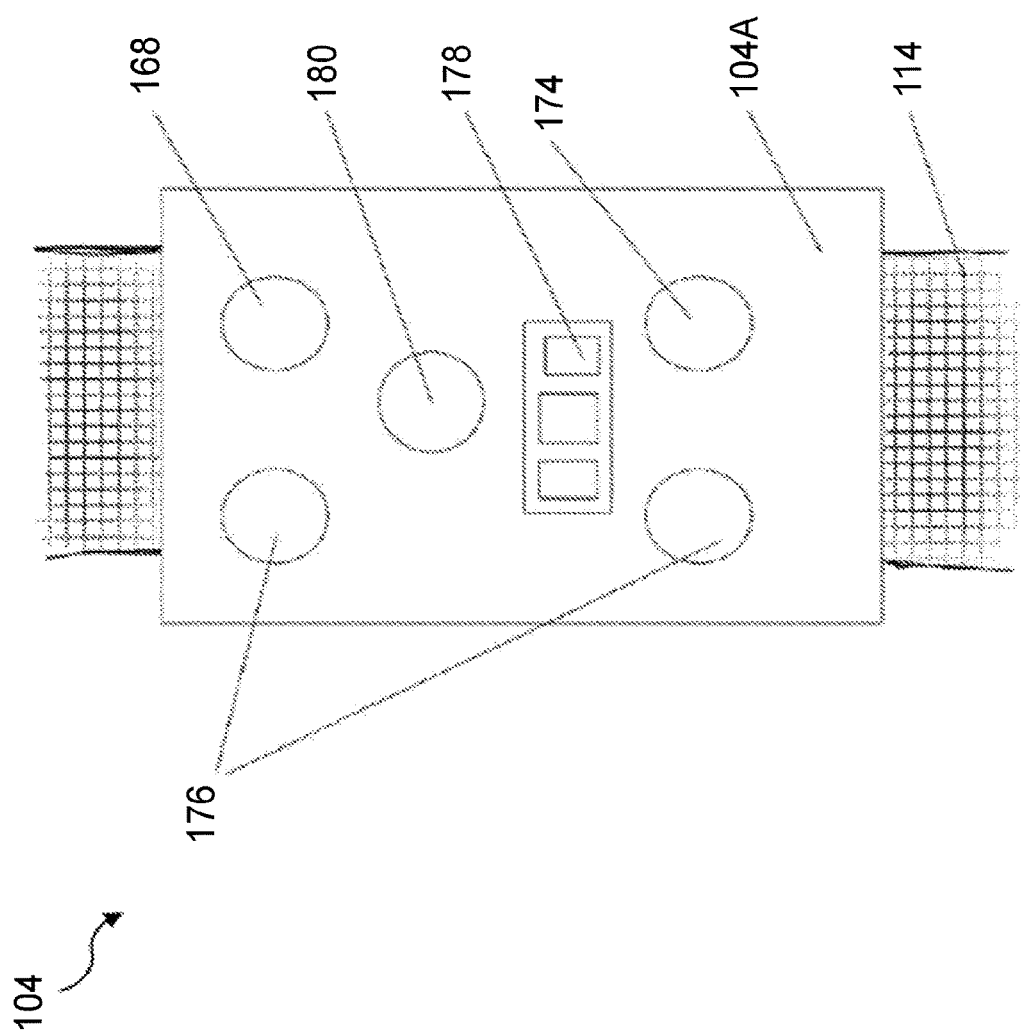

APPARATUS AND METHOD FOR DETERMINING PHYSIOLOGICAL PARAMETERS OF AN INFANT IN-UTERO

CROSS-REFERENCE TO RELATED APPLICATIONS

This application is a continuation of International Patent Application No.: PCT/US2020/056050, filed Oct. 16, 2020, which claims the benefit of priority to U.S. Provisional Application No. 62/916,094, filed on Oct. 16, 2019, each of which is incorporated herein by reference in its entirety.

FIELD

This application relates generally to medical instruments, and more specifically, to an apparatus for continuous monitoring of fetal conditions in-utero and methods of use thereof.

BACKGROUND

Fetal acidosis is a high level of acid in the blood of a fetus resulting from a limited oxygen supply available to the fetus over an extended period of time. Known tests for fetal acidosis, such as Doppler Ultrasonography, fetal heart rate monitoring, physical examination, and fetal blood tests are invasive or have unacceptable margins of error. For example, cordocentesis, an ultrasound-guided procedure to collect fetal blood from the umbilical cord, may not be used for routine or repeated monitoring due to its procedure-related risk.

Current fetal monitoring systems only monitor the heart rate of the fetus. Obstetric caretakers are forced to interpret heartrate signatures and guess if the baby is deprived of oxygen during labor. However, fetal heart rate monitoring alone has not proven to be a clinically viable diagnostic tool. Reliance on fetal heart rate monitoring alone has been determined to result in a 49% error rate in diagnosing when Cesarean procedures are needed. This error rate is determined by testing PH, SPO2, CO2, HCO3 levels from the umbilical cord blood after the baby is born and used to determine if the procedure was warranted. It is thus desired to be able to monitor the metabolic levels of the fetus during delivery to reduce the number of unnecessary c-sections.

Prior solutions that attempted monitor conditions of the fetus other than the heart rate were prone to failure and discontinued from use. One such solution is described in U.S. Pat. No. 4,281,659 and included pH sensors made with glass that were prone to breaking within the uterus of the mother. Use of such a device thus posed a risk to both the mother and the fetus. Moreover, the pH sensors of such prior solutions were prone to contamination via their porous glass membranes, thereby decreasing their efficacy. Due to these shortcomings, these devices were eventually discontinued from use in fetal monitoring.

A need exists for a procedure that is minimally invasive to the fetus but which allows medical professionals to reliably determine whether a fetus is experiencing fetal acidosis while a patient is in labor.

Moreover, existing procedures need to be performed each time the medical professional desires to determine a condition of the fetus. This is not only time consuming for medical professionals, but also burdensome for the patient to undergo each time a procedure is performed. Therefore, there is a need for continuous monitoring of the fetus without having to repeat medical intervention to reinsert a device to check the status of the fetus.

BRIEF DESCRIPTION OF THE DRAWINGS

FIG. 2B is a side view of the fetal sensor unit of FIG. 2A.

FIG. 2C is a cross-section view of the fetal sensor unit of FIG. 2A taken along lines 2C-2C of FIG. 2B.

FIG. 5B is a bottom view of the reference unit of FIG. 5A.

DETAILED DESCRIPTION

Generally speaking, described herein are systems, apparatuses, and methods to provide for continuous monitoring of one or more conditions of a patient. The patient condition monitoring systems described herein may include a sensor unit and a reference unit. The sensor unit may be removably affixed to the patient and take measurements related to conditions of the patient using one or more sensors. In some forms, one or more sensors of the sensor unit may be positioned within the skin when the sensor unit is affixed to the patient. The reference unit includes one or more sensors that provide reference signals for comparison with the sensor data generated by the one or more sensors of the sensor unit. The reference sensors may engage the outside of the skin of the patient or of another patient. The reference unit may display information based on the data received from the sensors. While the exemplary applications disclosed herein relate to monitoring various conditions of a fetus, those having skill in the art will appreciate that the sensor unit may adapted to monitor current conditions of any patient regardless of their age. For instance, the sensor unit may be affixed to a patients abdomen while the reference unit is affixed to the patient's arm. In other words, while oftentimes described herein as monitoring multiple patients, including a fetus, the structures and methods described herein may be used on a single patient with the sensors placed and/or inserted at various locations on the patient.

Figure 1A:
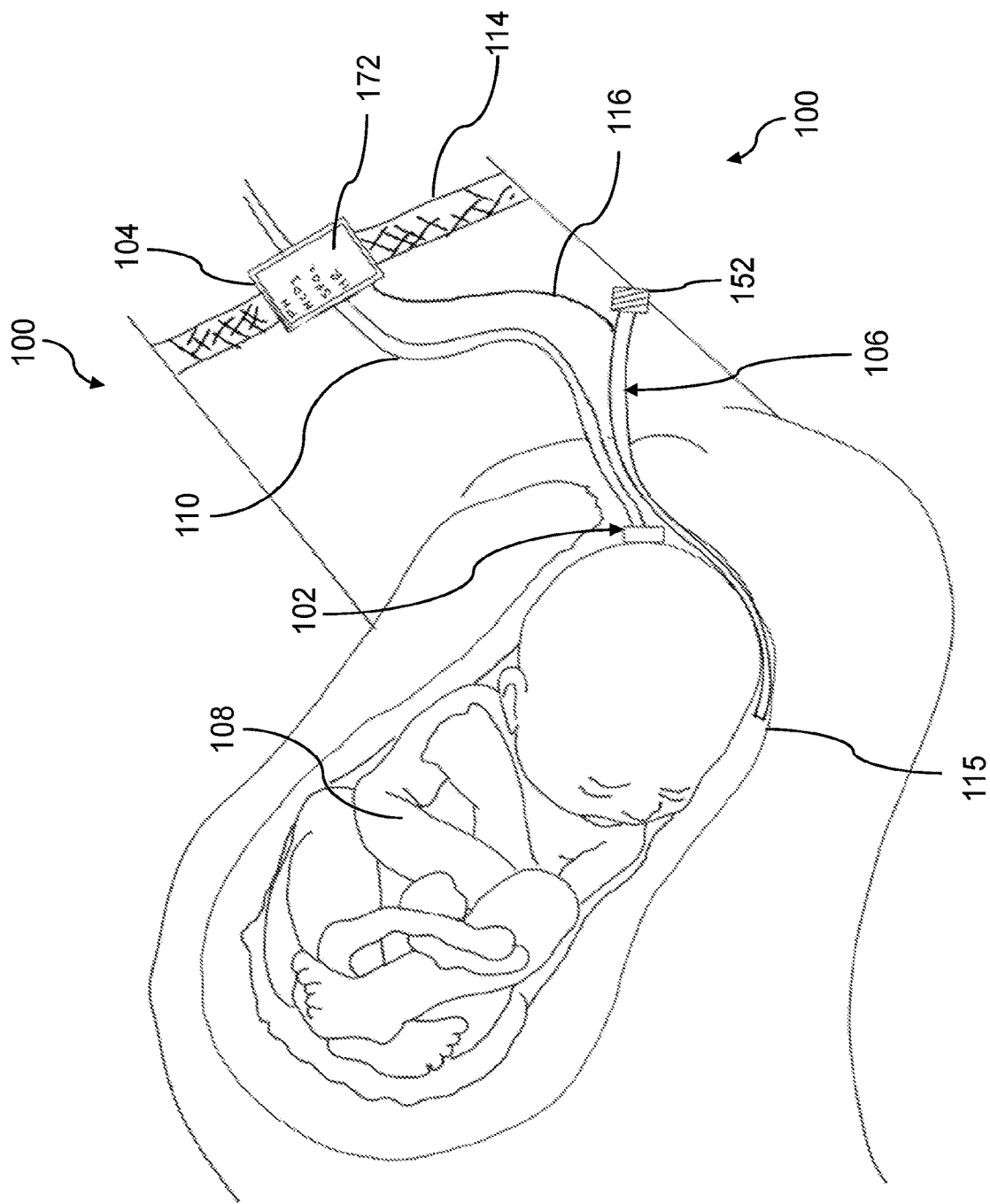
FIG. 1A is a partial cross-sectional view of a patient with a fetal condition monitoring system.

Referring now to the drawings, and particularly to FIG. 1, a fetal condition monitoring system 100 according to this disclosure is shown in use. In one form, the fetal condition monitoring system 100 includes a fetal sensor unit 102, a reference unit 104, and a pressure catheter 106. As shown, the fetal sensor unit 102 is attached to a fetus 108, i.e., an unborn infant. The fetal sensor unit 102 may be attached to the skin of the fetus, such as the scalp of the fetus, to measure one or more physiological conditions of the fetus 108 including temperature, heart rate, blood pH, blood oxygen saturation, and/or blood bicarbonate levels as examples.

As shown, the fetal sensor unit 102 is attached to the reference unit 104 via a wire harness 110. The wire harness 110 includes one or more conductors through which the fetal sensor unit 102 may receive electrical power and communicate sensor data to the reference unit 104. As shown, the reference unit 104 includes a display screen 172 that displays the measurements of the fetal sensor unit 102. In the embodiment shown, the reference unit 104 is mounted to the mother's body (e.g., thigh) via a strap or band 114, but the reference unit 104 may be positioned in other locations.

The pressure catheter 106 is positioned between the fetus 108 and the uterine wall 115 of the mother. The pressure catheter 106 includes a tube with a port 152 into which fluid may be input to provide an amniotic flush. The pressure catheter 106 may further include one or more pressure sensors to monitor the contractions of the mother. As shown, the pressure catheter 106 is attached to the reference unit 104 via a second wire harness 116. The wire harness 116 includes one or more conductors thorough which the sensors of the pressure catheter 106 receive electrical power and communicate sensor data to the reference unit 104. The pressure catheter 106 may also measure other conditions of the mother via the uterine wall such as, for example, pH and bicarbonate levels.

Figure 1B:
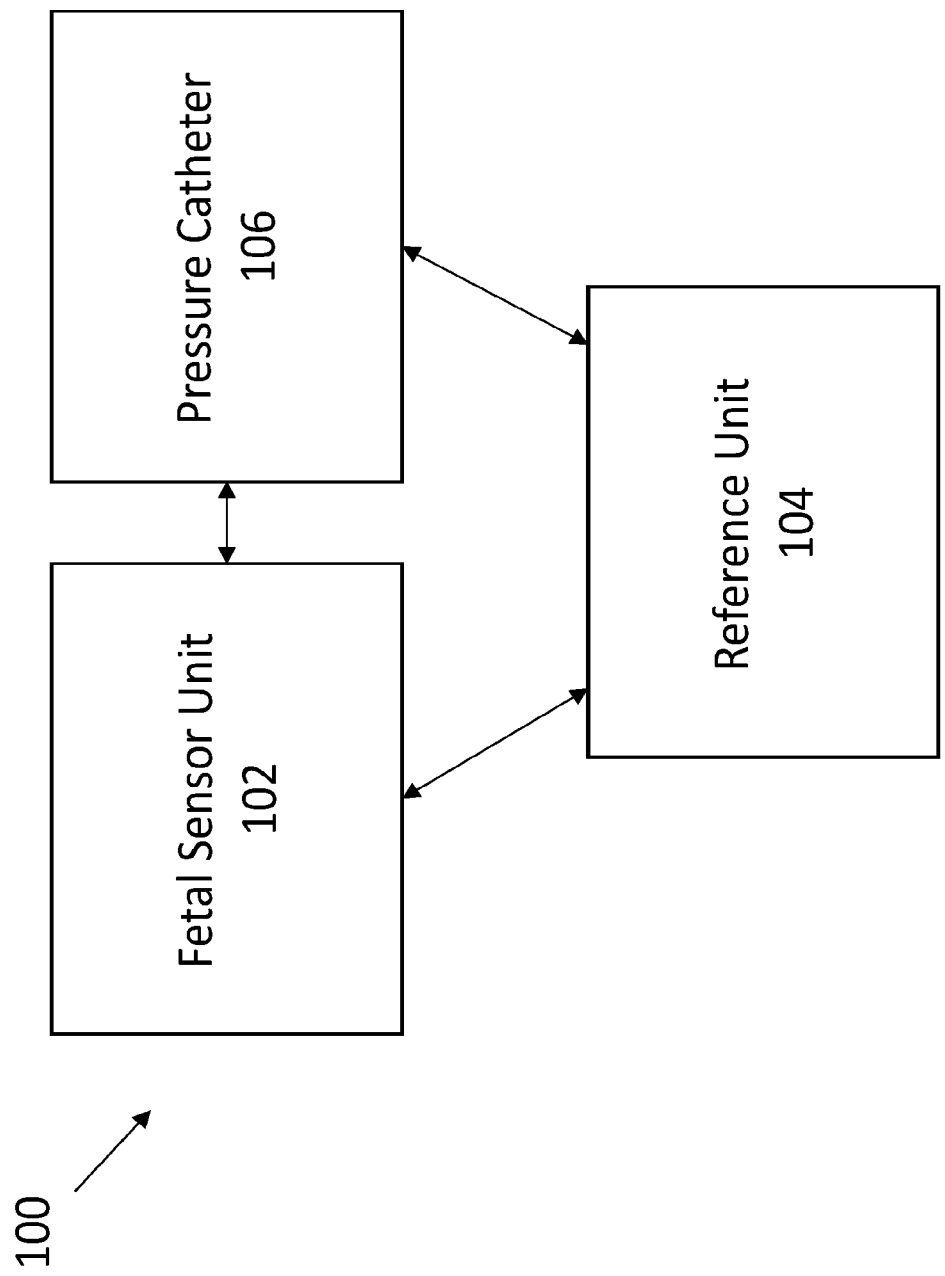
FIG. 1B is a block diagram showing the communication between the various components of the fetal condition monitoring system.

With reference to FIG. 1B, the fetal sensor unit 102, the reference unit 104, and the pressure catheter 106 of the fetal monitoring system 100 may communicate with one another via wired and/or wireless communication protocols. In the embodiment shown in FIG. 1A, the sensor unit 102 communicates with the reference unit 104 via the wire harness 110 and the pressure catheter 106 communicates with the reference unit 104. The reference unit 104 may facilitate communication between the fetal sensor unit 102 and the pressure catheter 106. In other embodiments, the fetal sensor unit 102, the reference unit 104, and the pressure catheter 106 may communicate with one another via one or more of wireless fidelity (Wi-Fi), Cellular, radio frequency (RF), infrared (IR), Bluetooth (BT), Bluetooth Low Energy (BLE), Zigbee, near field communication (NFC), and/or other wireless methods.

Figure 2A:
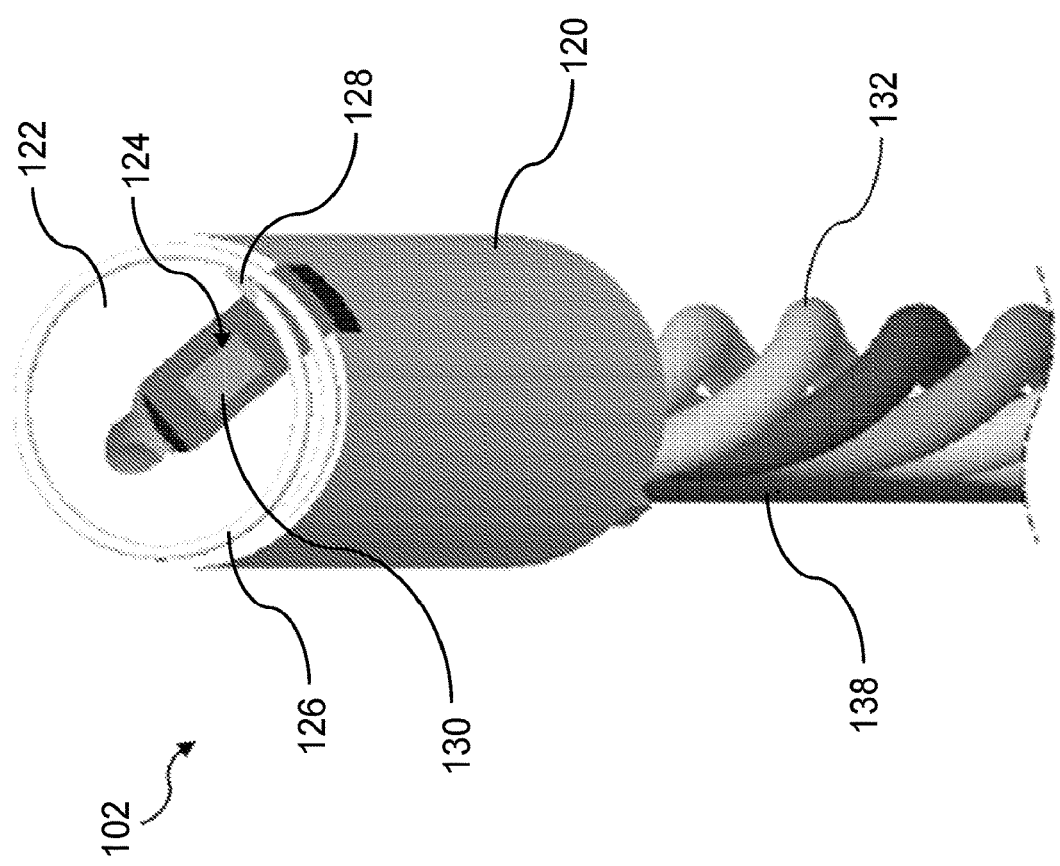
FIG. 2A is a top perspective view of a fetal sensor unit of a fetal condition monitoring system according to a first embodiment.
Figure 2D:
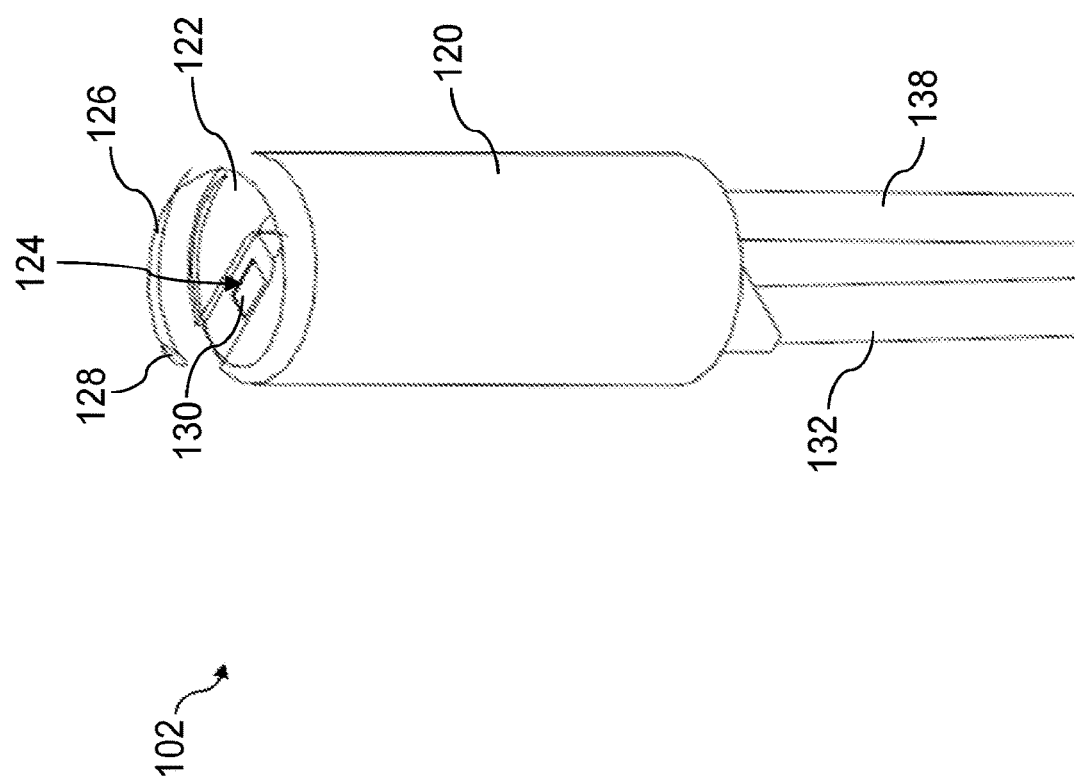
FIG. 2D is a top perspective view of the fetal sensor unit of FIG. 2A.

With reference to FIGS. 2A-C, the fetal sensor unit 102 is shown according to a first embodiment. The fetal sensor unit 102 includes a cylindrical body 120 formed of a high-density polyethylene, silicone, low-density polyethylene, synthetic polyisoprene, polyurethane, nitrile, thermoplastic elastomers and polymers or another medical grade polyethylene or polymer. In some forms, the body 120 may be rigid, such as having little to no flex, or semi-rigid, such has having some flex.

The cylindrical body 120 includes an attachment end 122 at the base of the cylinder body 120 that includes an attachment mechanism for affixing the body 120 of the fetal sensor unit 102 to the fetus and one or more sensors 124. The attachment mechanism may be configured to pierce the skin of the fetus to attach the body 120 to the fetus. A portion of the attachment mechanism remains underneath or within the skin thereby affixing the body 120 to the fetus. The attachment mechanism may be a helical or spiral wire 126 extending away from the attachment end of the body 120. The spiral wire 126 includes a sharp or angled tip 128 that enables the spiral wire 126 to pierce the skin of the fetus. In use, the tip 128 is brought into contact with the skin of the fetus and may be pressed into the skin of the fetus to pierce the skin. The body 120 of the fetal sensor unit 102 may then be rotated to feed or embed the spiral wire 126 into the skin of the fetus and draw the attachment end 122 toward the skin of the fetus. Once the helical wire 126 is firmly embedded into the skin of the fetus 108, the fetal sensor unit 102 is affixed to the fetus 108. Using the spiral wire 126 to attach the fetal sensor unit 102 to the fetus aids to prevent the fetal sensor unit 102 from shifting, migrating, or otherwise becoming detached from the fetus which may result in damage to tissue of the fetus 108 or the mother. Moreover, the use of a spiral wire 126 to attach the fetal sensor unit 102 allows the attachment end 122 to be drawn toward the skin of the fetus 108 which brings one or more sensors of the attachment end 122 into engagement with the skin of the fetus 108.

The attachment end 122 further includes one or more sensors 124 for monitoring a condition of the fetus. The condition of the fetus may be a physiological parameter of the fetus such as, for example, temperature, heart rate, blood pH, blood oxygen saturation, and/or blood bicarbonate levels. The sensors 124 of the attachment end 122 may include a pH sensor 130 configured to detect pH. Once the fetal sensor unit 102 is attached to the fetus 108, the pH sensor 130 contacts the surface of the skin of the fetus 108. The pH sensor 130 is then able to collect pH data of the fetus 108 which may be used to detect a condition of the fetus such as, for example, fetal acidosis. The attachment end 122 may further include sensors configured to collect or measure other aspects relating to the health or condition of the fetus 108. Examples of such sensors include a heart rate monitor or ECG sensor for detecting the heart rate of the fetus 108, a thermometer for measuring the temperature of the fetus 108, an pulse oximetry sensor for measuring the oxygen saturation levels (SPO2) of the blood or the fetus 108, and a bicarbonate sensor for measuring bicarbonate levels in the blood of the fetus 108. These sensors may be mounted to the attachment end 122 of the body 120 of the fetal sensor unit 102 and be brought into contact with the fetus 108 upon attachment of the body 120 to the fetus 108 via the spiral wire 126. In other forms, one or more sensors are mounted to the spiral wire 126 of the attachment end 122 such that upon attachment of the body 120 to the fetus, the sensors are within and/or underneath the skin of the fetus. The sensors 124 may receive power from a power cable of the wire harness 110 extending from the body 120 to the reference unit 104. Alternatively or additionally, the body 120 may contain a power source, such as a battery, to power the sensors 124.

In some forms, the pH sensor 130 includes a temperature sensor either built into the pH sensor 130 or separate but associated with the pH sensor 130. The temperature sensor can be used to help maintain an accurate reading for the pH sensor. Various types of pH sensors can be used including, but not limited to ISFET pH (ion-sensitive field-effect transistor) sensors and the like. As described above, prior sensors were typically built with glass or other materials that were not generally appropriate for the small size necessary for internal monitoring. The fabrication of ISFET sensors using new methods including, but not limited to, light curable materials allows the small size and accuracy while minimizing the risk of injury to the mother and/or fetus. The ISFET sensors may be built with ChemFET sensors layered on top of the pH gate. This allows for sensing chemical signatures in combination with pH.

Certain pH sensors, such as ISFET sensors are susceptible to light interfering with detection and accuracy. In this regard, other sensors, such as pulse oximetry sensors that emit various forms of light, can interfere with the pH sensors. Therefore, in some forms, the devices may be configured that the pH sensor and pulse oximetry emitter/sensor cycle such that they are not detecting at the same points in time. In some forms, the light emitters may be ionized to benefit the ion transport.

The sensors 124 of the fetal sensor unit 102 may also include a bicarbonate sensor. The bicarbonate sensor may take a variety of forms, such as a bicarbonate ISFET sensor. The sensor can be augmented by modifying the filter materials for ion exchange. pH of the blood is a well-known metric for determining acidosis or lack of oxygen. The metabolic process of an oxygen deprived body will create acid. The increased acid causes the blood pH to change. To prevent cellular damage the body maintains bicarbonate as a buffer to mitigate cellular damage and or death. Thus, inclusion of a bicarbonate sensor aids a practitioner in identifying the condition of the fetus based on the blood, by identifying bicarbonate levels in combination with the blood pH. For instance, when the acidity of the blood is high and/or increasing and the bicarbonate levels are also rising, this may confirm the presence of fetal acidosis. Knowing the current bicarbonate levels in addition to the pH of the blood may also aid the practitioner in determining the ability of the fetus to recover.

The pulse oximetry sensor can be a single sensor and/or comprise separate components. In some forms, the pulse oximetry sensor can include an emitter, such as LEDs or IR emitters, and detectors, such as photo diodes. There are two main types of pulse oximetry sensors, reflective and transmissive. Reflective sensors emit and receive from generally the same surface relative to the patient. Transmissive, on the other hand, will emit on one side of the patient's tissue and receive on the other. The devices herein can include both types of pulse oximetry sensors. The emitter may include Light Emitting Diodes (LEDs) that emit light of different peak emission wavelengths, including, but not limited to, infrared light. The light may pass through the fetus's skin may be reflected off the fetus's subcutaneous bone and tissue before being received by the photodetector. The change in absorbance of the light emitted at each wavelength may be correlated to the level of oxygen saturation in the fetus's blood. The rate of change of the absorbance may be correlated to the observed pulse rate, which may be used to confirm contact with the fetus. For example, if the observed pulse rate is high as compared to the external pulse rate of the pregnant person, then contact with the fetus may be confirmed. For example, during labor, a pregnant person may have a pulse rate of 118 beats per minute, and the observed pulse rate may be 145 beats per minute, which may confirm contact with the fetus.

Further, the fetal sensor unit 102 may determine if the sensors are in contact with the patient, and then switch to transmissive sensing. As noted above, in some forms, the pulse oximetry needs to cycle relative to pH sensing so that the light emitted from the pulse oximeter does not interfere with the pH sensing. Other sensors using refraction detection of one or more spectrums of light may also need to be cycled so the light does not interfere with other sensors, such as the pH sensor.

The sensors 124 may communicate the data collected via one or more communication conductors, such as wires 132, to a processing device. In the embodiment shown, the sensors 124 communicate the data to the reference unit 104 via wires 132 that extend from the sensors 124, through a channel 134 of the body 120, out an end 136 of the body 120 opposite the attachment end 122, and to the reference unit 104. The wires 132 extending to the reference unit 104 from the fetal sensor unit 102 form the wire harness 110. As shown, the wires 132 may be twisted about each other which may aid to reduce electromagnetic interference between the wires. In other forms, the wires 132 are not twisted. In some forms, the wires may be covered by and extend through a protective sheath. The sheath may be formed of a plastic or rubber material. The sheath may aid to hold the wires 132 together and provide additional insulation and protection from fluids the fetal condition monitoring system 100 encounters.

In an alternative embodiment, the fetal sensor unit 102 is wireless and the body 120 includes a processor and memory configured to process and record the sensor data. The body 120 may also include a battery to power the sensors and the other electrical components. The body 120 may further contain communication circuitry configured to communicate with the reference unit 104 via a wireless protocol. The processor may communicate the sensor data to the reference unit 104 via the communication circuitry. As examples, the communication circuitry may be configured to communicate via one or more of wireless fidelity (Wi-Fi), Cellular, radio frequency (RF), infrared (IR), Bluetooth (BT), Bluetooth Low Energy (BLE), Zigbee and near field communication (NFC).

Figure 3:
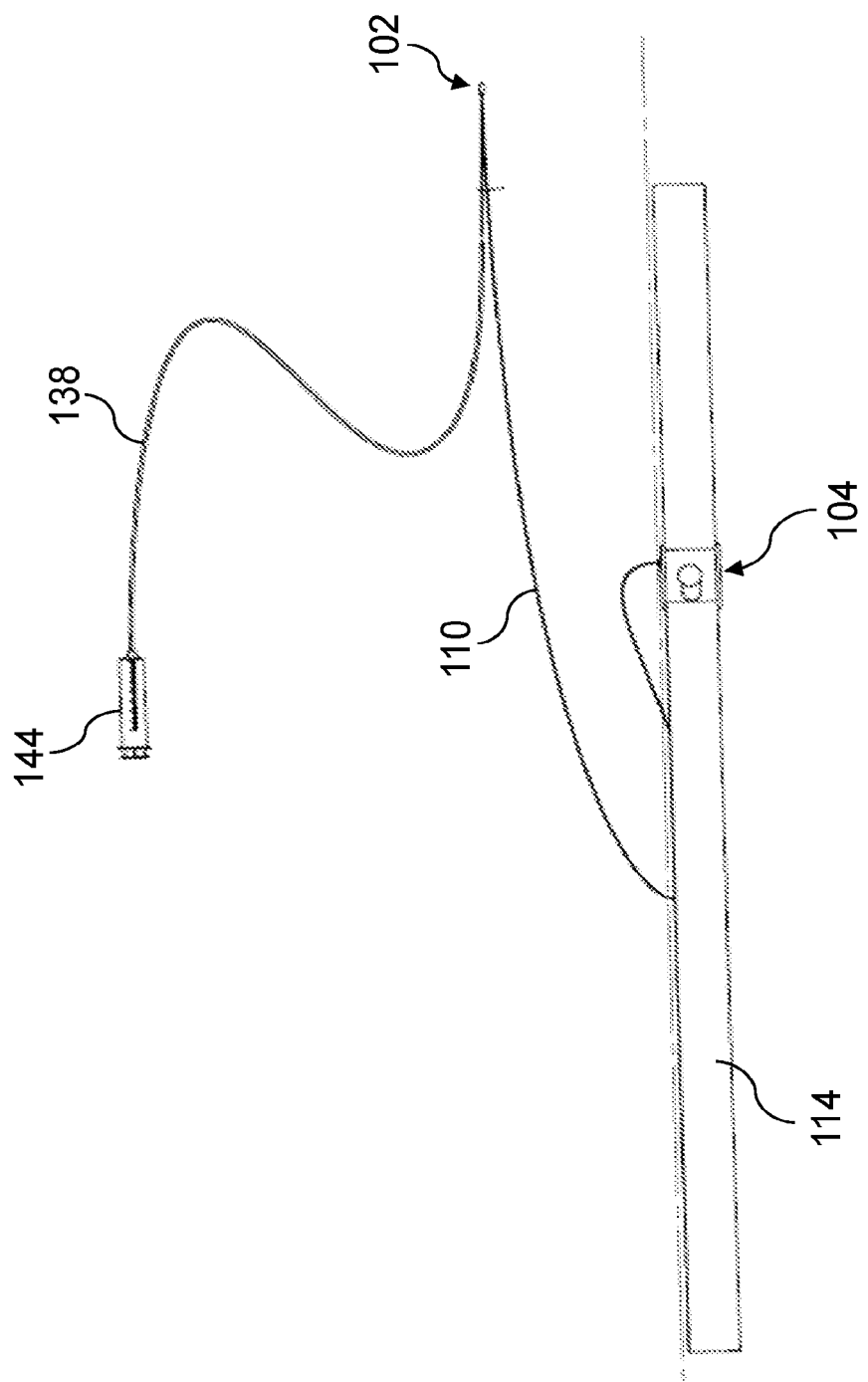
FIG. 3 is a side view of a fetal sensor unit with a syringe connected thereto.

The body 120 of the fetal sensor unit 102 further defines a channel 140 through which fluid may pass through the body 120. As shown, a tube or hose 138 extends into the channel 140 of the body 120 to a fluid dispensing opening 142 in the attachment end 122. The hose 138 may be connected to fluid source containing, for example, deionized water. With reference to FIG. 3, the fluid source is a syringe 144 connected to the end of the hose 138 opposite the fetal sensor unit 102. During use of the fetal condition monitoring system 100, a fluid may be forced through the hose 138 and out the dispensing opening 142. For example, the syringe 144 may be used to force fluid through the hose 138, through the body 120, and out the dispensing opening 142. When the fetal sensor unit 102 is attached to the fetus 108, the fluid may be used to flush or clean the area of the fetus that the sensors 124 engage. As shown in FIG. 2C, the channel 140 may include an angled segment 140A that directs or guides the water toward the sensors 124. The fluid forced through the hose 138 may be deionized water to eliminate contamination readings. Deionized water or fluid is devoid of ions and reduces the likelihood of false readings by the sensors 124. Moreover, providing a deionized water flush helps to remove contaminates and also creates a conduit for ions to travel from the tissue to the sensor. Providing such a fluid channel with the deionized water or fluid aids in the functioning of ISFET pH and Chemical sensors that may be mounted to the attachment end 122 of the body 120. In another form, the end 136 of the body 120 may include a port configured to connect to the hose 138. Fluid may then flow from the hose 138 and into the channel 140 via the port.

Figure 4:
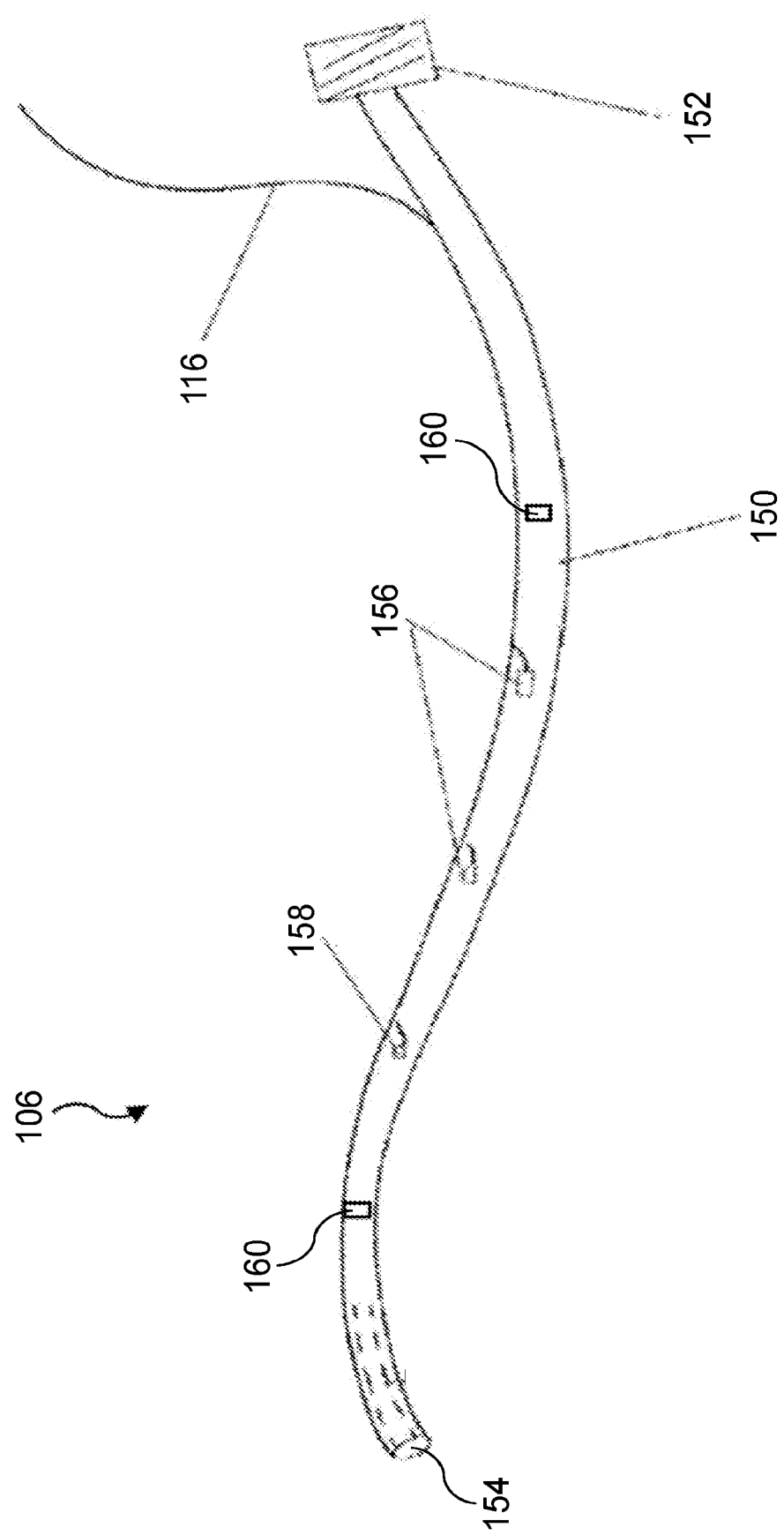
FIG. 4 is a side view of a pressure catheter of a fetal condition monitoring system.

With reference to FIG. 4, the pressure catheter 106 includes a tube 150. The tube 150 is a flexible tube that may be formed of a rubber, silicone, metal, plastic or a combination thereof. The tube 150 may be hollow thus forming a channel for fluid to flow through. The tube 150 includes a port 152 into which the fluid may enter the tube 150. Fluid may be injected into the tube 150 through the port 152 via a syringe. The port 152 may include a one-way valve permitting fluid to enter the tube through the port 152, but inhibiting fluid from exiting the tube 150 via the port 152. The tube 150 includes an open end 154 through which the fluid may exit the tube 150.

The pressure catheter 106 may further include sensors disposed along the body of the tube 150 for monitoring the contraction pressure of the mother and other uterus biomarkers. For example, the pressure catheter 106 may provide data on uterine muscle conditions. An increase in lactate and lactic acid concentrations in in uterine and surrounding muscle tissue limits the uterine muscle contraction force. Thus knowing the amount of lactate or lactic acid in uterine and surrounding muscle tissue may be useful in making clinical decisions regarding the delivery of the fetus.

In the embodiment shown in FIG. 4, the pressure catheter 106 includes two pH sensors 156, a bicarbonate sensor 158, and two pressure sensors 160. These sensors may operate similar to the sensors described above in regard to the fetal sensor unit 102. In other forms, the pressure catheter 106 may include any number of pH sensors 156, bicarbonate sensors 158, and pressure sensors 160 disposed along the tube 150. In other embodiments, the pressure catheter 106 may further include one or more sensors for measuring ECG of the mother and/or the fetus, blood oxygen sensors, ChemFET sensors, ion detection sensors, and/or photoacoustic sensors. These sensors may be electrically coupled to one or more conductive wires or pathways forming the wire harness 116. In the embodiment shown, the wire harness 116 extends from the pressure catheter 106 to the reference unit 104. The reference unit 104 may provide electrical power to the sensors of the pressure catheter 106 via the wire harness 116 enabling the sensors to capture sensor data. The sensors may communicate the sensor data captured through the wires of the wire harness 116 to a processing device, such as a processing device of the reference unit 104. The processing device may analyze the data provided by the sensors to determine one or more conditions of the health of the mother and/or the fetus. For instance, the processing device may use the data provided by the pressure sensors 160 to determine the contraction pressure and the contraction rate of the mother which may be useful in making clinical decisions regarding the delivery of the fetus.

In other forms, the pressure catheter 106 may be independent of the reference unit 104 such that the pressure catheter 106 is not connected to the reference unit 104 via the wire harness 116. In these forms, the pressure catheter 106 may have its own power source (e.g., a battery or power supply) that powers the sensors. The sensors may be electrically coupled to the power source via a wire harness. The pressure catheter 106 may communicate the sensor data to a processing device that may display, output, store and/or analyze the sensor data. In some forms, the pressure catheter 106 includes communication circuitry configured to communicate with the reference unit 104 or a remote computer via a wireless connection such as one or more of wireless fidelity (Wi-Fi), Cellular, radio frequency (RF), infrared (IR), Bluetooth (BT), Bluetooth Low Energy (BLE), Zigbee and near field communication (NFC).

In use, the tube 150 is placed in between the skin of the fetus and the uterine wall of the mother. An amniotic flush may be provided via the pressure catheter 106 by inputting fluid into the tube 150 via the port 152. Fluid may be input into the tube 150 via a syringe as an example. The fluid travels along the channel within the tube 150 and exits the tube 150 at the open end 154 and into the uterus of the mother, thus providing an amniotic flush. The exterior of the tube 150 may include one or more layers of material to which the sensors of the pressure catheter 106 are mounted and any conductors associated with the sensors may be connected. As described in further detail below, the sensors (e.g., pH sensors 156, bicarbonate sensor 158, and pressure sensors 160) capture data that may be processed, for example by the reference unit 104, to monitor one or more conditions of the fetus 108 and the mother including ECG, heart rate, pH, bicarbonate levels, contraction pressure, and contraction rates of the mother and/or fetus. For example, the pH sensors 156 may monitor the lactate buildup on uterine wall. Based on the pH data provided by the pH sensors 156, the amount of Pitocin administered to the mother may be regulated to prevent an overuse of Pitocin in starting contractions.

With reference to FIGS. 5A-5D the reference unit 104 of the fetus condition monitoring system 100 is shown. The reference unit 104 receives the sensor data from the fetal sensor unit 102 and the pressure catheter 106. As described above, the fetal sensor unit 102 may be communicatively coupled to the reference unit 104 via the wire harness 110 and the pressure catheter 106 may be communicatively coupled to the reference unit 104 via the wire harness 116. The reference unit 104 may include a series of ports 170 into which one or more cables of the wire harness 110 and/or wire harness 116 may be inserted to provide electrical power to and/or receive sensor data from the fetal sensor unit 102 and the pressure catheter 106. The reference unit 104 includes a processor and a memory and processes and/or stores the data received from the fetal sensor unit 102 and the pressure catheter 106. The reference unit 104 may further include communication circuitry for communicating the sensor data and/or any information determined based on the sensor data to a remote computer. The communication circuitry may be configured to communicate via one or more of wireless fidelity (Wi-Fi), Cellular, radio frequency (RF), infrared (IR), Bluetooth (BT), Bluetooth Low Energy (BLE), Zigbee and near field communication (NFC).

In one form, the reference unit 104 houses a battery 164 for powering the reference unit 104 and the fetal sensor unit 102 and pressure catheter 106. The reference unit 104 includes a charging port 166 for charging the battery 164 without having to remove the battery 164 from the reference unit. In other forms, the battery 164 is removed from the reference unit 104 and replaced or recharged. A charged battery 164 may be inserted into the reference unit 104 for powering the fetal condition monitoring system 100. In yet other forms, the reference unit 104 receives power via a power cord. In one example, the reference unit 104 includes a port for receiving a jack of the power cord. The power cord may deliver electrical power to the reference unit 104 via a wall outlet, for example.

In the embodiment shown in FIGS. 5A-D, the reference unit 104 includes one or more sensors or electrodes for monitoring or measuring health conditions of the mother. These sensors may operate similarly to the sensors described in regard to the fetal sensor unit 102. The reference unit 104 may be configured to be mounted or affixed to the mother such that the sensors or electrodes engage the skin of the mother to enable the sensors to capture data from the mother. The reference unit 104 may be affixed to the mother's body via a strap or band 114. The strap 114 may wrap around the mother's body and be cinched to firmly affix the reference unit 104 to the mother. As shown in FIG. 1, the reference unit 104 is attached via the strap 114 to the mother's leg (e.g., thigh). In other forms, the reference unit 104 is affixed to other portions of the mother's body, such as the mother's arm or abdomen as examples. In other embodiments the reference unit 104 is attached to the mother via an adhesive or tape.

As shown in FIG. 5B, the bottom 104A of the reference unit 104 includes a pH sensor 168, a bicarbonate sensor 174, an ECG monitor 176, a blood oxygen saturation sensor 178, and an ECG fetal reference sensor 180. The bottom 104A of the reference unit 104 may be brought into contact with the outer surface of the mother's skin to collect data from the mother via the sensors. This data collected from the various sensors or electrodes of the reference unit 104 may be compared with sensor data collected from the fetal sensor unit 102 and pressure catheter 106. When reference data is not used, the sensor data provided by the sensors of the fetal sensor unit 102 and pressure catheter 106 may be inaccurate because they are prone to drift or variation without comparison to a reference signal. Using the data provided by the sensors of the reference unit 104, a condition (e.g., pH, bicarbonate, oxygen saturation, etc.) may then determined with increased accuracy. Moreover, since the reference unit 104 is not mounted to the fetus along with the fetal sensor unit 102 inside the uterus of the mother, the reference unit 104 and the sensors thereof are accessible for cleaning and sanitation. This is advantageous over systems where the reference sensors engage the outer surface of the skin of the fetus where the component including the reference sensors would have to be withdrawn from the uterus of the mother to clean the reference sensors for recalibration.

In another example, the processor of the reference unit 104 may compare the ECG reading of the mother with the ECG reading of the fetus. As described above, the reference unit 104 includes an ECG sensor for capturing ECG data from the mother and the fetal sensor unit 102 includes a sensor for capturing ECG data of the fetus. If the ECG data collected from both the mother and the fetus are substantially the same, the processor may be configured to determine that the fetal sensor unit 102 is capturing ECG data from the mother rather than the fetus.

The reference unit 104 may likewise use the sensor data from the mother as reference data with which the sensor data collected from the fetus 108 is compared. For example, if the data output by the pH sensor of the fetal sensor unit 102 indicates the blood of the fetus 108 is abnormally low (e.g., less than 6.2), but the data is similar to the pH data of the mother, the reference unit 104 may be configured to determine that the pH sensor is out of calibration and the acid level of the blood of the fetus 108 may be normal. The reference unit 104 may similarly compare the fetal sensor unit 102 output data with corresponding data collected from the mother by the reference unit 104 to aid to determine when the fetal sensor unit 102 is out of calibration to reduce the number of false indications of abnormal or alarming fetal conditions.

Figure 5A:
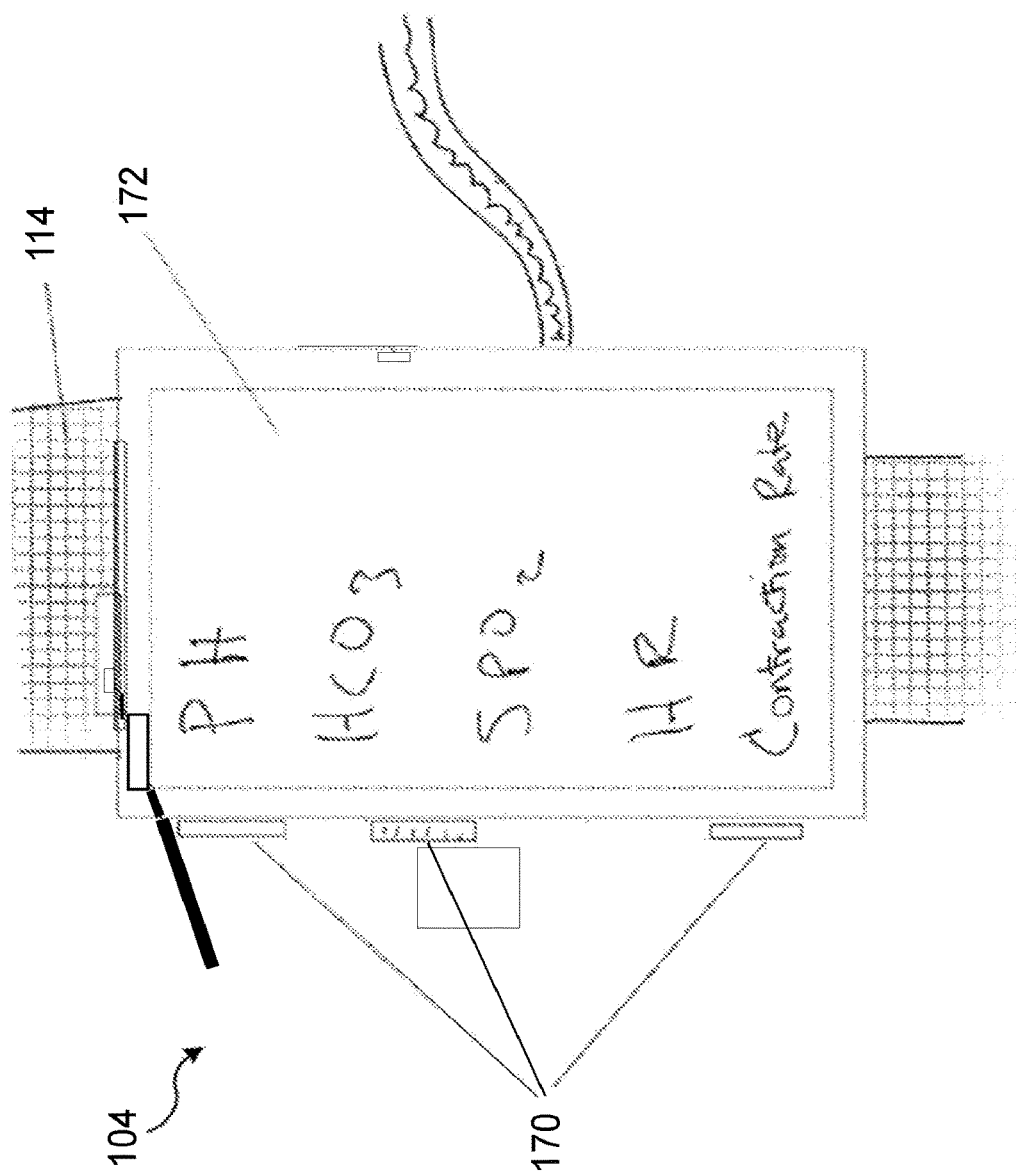
FIG. 5A is a top view of a reference unit of a fetal condition monitoring system.
Figure 5C:
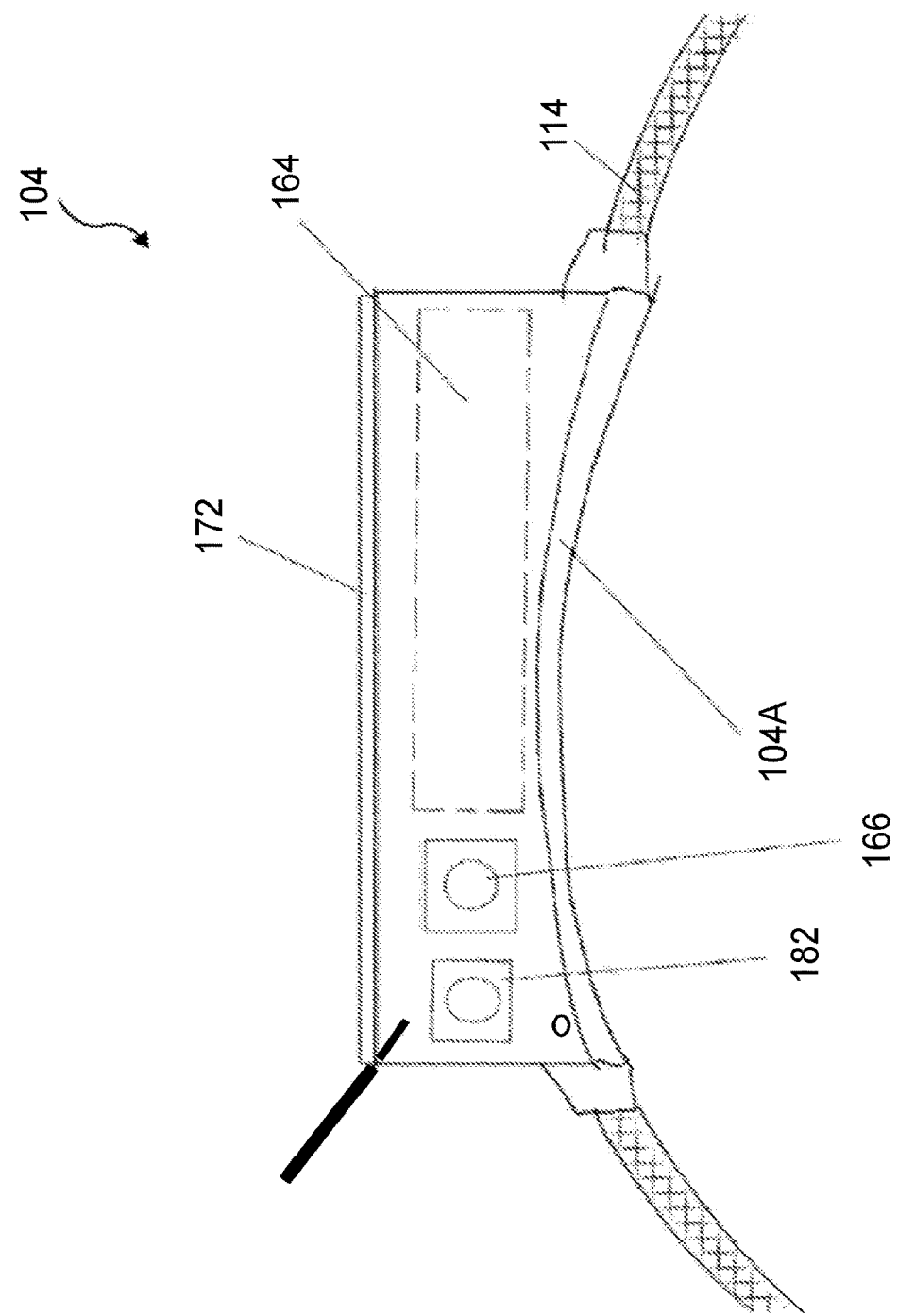
FIG. 5C is a right side elevation view of the reference unit of FIG. 5A.
Figure 5D:
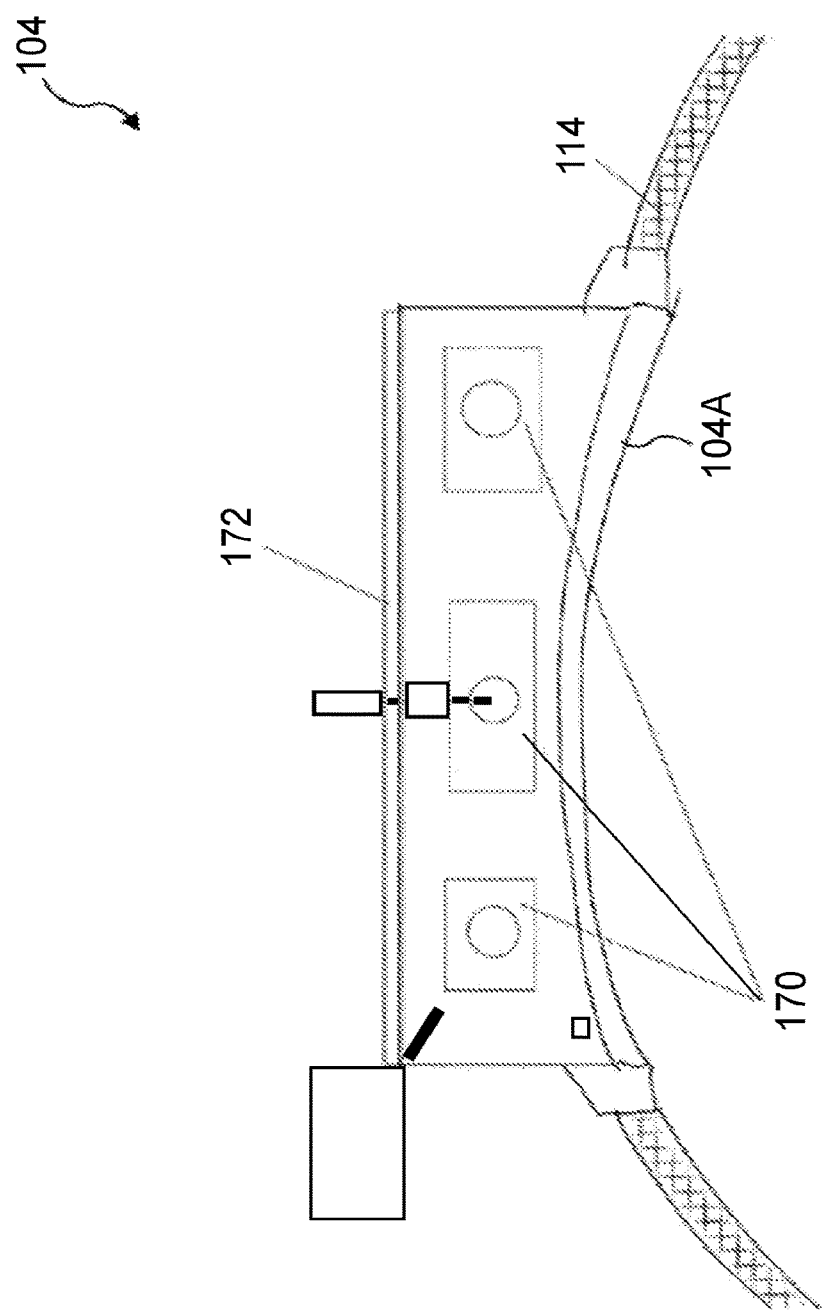
FIG. 5D is a left side elevation view of the reference unit of FIG. 5A.

As shown in FIGS. 5C-D, the bottom 104A of the reference unit 104 is curved. Including a curvature on the bottom 104A enables the bottom 104A of the reference unit 104 to engage a larger surface of a curved portion of the mother's body, for instance, the mother's arm or leg to which the reference unit 104 is affixed. The bottom 104A of the reference unit 104 maybe formed of a flexible material such as rubber, silicone, and/or various densities of plastic to enable the bottom 104 of the reference unit 104 to conform to the portion of the mother's body to which the reference unit 104 is affixed. This ensures that the sensors are brought into contact with and engage the skin of the mother's body to aid in capturing accurate readings via the sensors.

In the embodiment shown, the reference unit 104 includes a display screen 172 that is configured to display health status information of the mother and/or the fetus. The processor of the reference unit 104 may receive the sensor data from the fetal sensor unit 102, the pressure catheter 106 and the reference unit 104 sensors and display the sensor output on the display screen 172. The sensor output may include sensor data that has been processed and/or compared to the corresponding data collected by the sensors of the reference unit 104. As one example shown in FIG. 5A, the reference unit 104 may be configured to display the data collected from the sensors of the fetal sensor unit 102 and/or the pressure catheter 106. For instance, the display screen 172 may show the current heart rate, the blood pH level, the blood bicarbonate level, and/or the blood oxygen saturation level of the fetus. The display screen 172 may also display the current heart rate, the blood pH level, the blood bicarbonate level, the blood oxygen saturation level, contraction rate, and/or contraction pressure of the mother.

The reference unit 104 may further be configured to process the data received from the various sensors to monitor the health of the fetus 108 and to alert the user when the condition of the fetus changes. The pH of the blood is a well-known metric for determining acidosis or lack of oxygen. The metabolic process of an oxygen deprived body will create acid. The increased acid causes the blood pH to change. A change in pH of the fetus's blood may thus be indicative of complications in oxygen delivery and may lead to further problems, such as fetal acidosis. Likewise, a change in the oxygen saturation levels of the blood may be indicative of asphyxiation of the fetus and/or fetal acidosis. A change in the bicarbonate level of the blood indicates a change in the metabolic state of the fetus. The reference unit 104 may be configured to indicate when an abnormal condition is present based on the values or trends of the sensor data received from the reference unit 104. The reference unit 104 may come programed with the values or data trends that are determined to be abnormal or the values may be set by a medical professional, such as a nurse or doctor. The reference unit 104 may be configured to monitor changes and trends in the sensor data over time and determine whether a change in the sensor data indicates a change in a condition of the fetus (e.g., fetal acidosis). The reference unit 104 may be configured to monitor multiple aspects of the fetus to arrive at a determination of a change in the condition of the fetus. For instance, a diagnosis of fetal acidosis where the sensor data indicates an abnormal range of pH values associated with fetal acidosis or an elevated range where fetal acidosis is more likely may be further supported by a low oxygen saturation level in the fetus's blood, e.g. a oxygen saturation level of less than about 58%, or a high fetal pulse rate, e.g., a fetal pulse rate over 160 beats per minute. In one form, a diagnosis of fetal acidosis may also depend on the changing trend in pH, oxygen saturation level, or pulse rate of the fetus if multiple measurements are taken.

In some forms, the reference unit 104 may be configured to display values via the display screen 172 in red if they are abnormal and/or require intervention. In some embodiments, the display screen 172 is configured to display one or more of the sensor outputs for a period of time and then change the display screen 172 to show other sensor outputs. For instance, the display screen 172 may show the health status information of the fetus for ten seconds and then switch to display the health status information of the mother for ten seconds. In some forms, the display screen 172 may display only health status information that is abnormal or requires action. For example, if the pH level of the blood of the fetus is too low, the display screen may display the current blood pH level. As another example, if the reference unit 104 is not able to determine a heart rate of the fetus, the reference unit 104 may display that the fetal sensor unit 102 needs to be serviced. The reference unit 104 may also be configured to display the diagnosed problem or condition on the screen 172. For example, if the pH of the blood of the fetus continuously decreases for a period of time (e.g., one minute) the reference unit 104 may be configured to display or flash that the fetus may have fetal acidosis to indicate that intervention is required.

The reference unit 104 may further include a display auxiliary port 182 used to connect the reference unit 104 to an alternative monitor or display. A cable may be connected to the reference unit 104 and the alternative monitor or display to cause the data of the sensors to be displayed via the alternative monitor or display.

In some forms, the reference unit 104 may include one or more lights or LEDs used to indicate the condition of the mother and/or the fetus. For instance, an LED of the reference unit 104 may display a green light when the condition of the fetus is OK, yellow when the condition of the fetus is near a threshold value indicating a condition of the fetus needs to be monitored closely, and red when an abnormal or alarming condition is present requiring intervention. The reference unit 104 may include such an LED for each monitored aspect of the fetus (e.g., blood oxygen level, heart rate, blood pH level, etc.). The reference unit 104 may further include a speaker, buzzer, or vibrator that is used to indicate when an abnormal or alarming condition is present and that intervention or review by medical staff needs to occur. In some forms, the reference unit 104 does not include a display screen 172 but rather includes only one or more alternative display forms such as the indicator lights, speaker, buzzer, or vibrator.

In some forms, the processor of the reference unit 104 may communicate the sensor data to a remote computer (e.g., a server computer) via the communication circuitry for processing and or storage. The reference unit 104 via the communication circuitry and/or the remote computer may be configured to send an alert or notify medical personnel when the sensor data indicates an abnormal or alarming condition is present in the mother or fetus. For instance, the reference unit 104 may send a text message to or cause a notification to be pushed to a computing device (e.g., via a cell phone application) of a nurse, doctor, or health system administrator as examples. The reference unit 104 may be configured to communicate sensor data to a remote computer for processing and receive a signal from the remote computer indicating what should be displayed via the reference unit 104.

In operation, the fetal condition monitoring system 100 is used to monitor various conditions of the fetus when the mother is in labor. The body 120 of the fetal sensor unit 102 is inserted into the uterus of the mother and affixed to the skin of the fetus 108. The tip 128 of the spiral wire 126 may be brought into contact with the skin (such as the scalp) of the fetus 108. The body 120 and/or the spiral wire 126 may then be rotated such that the tip 128 of the spiral wire 126 pierces the skin of the fetus 108. The body 120 may be rotated to continue to feed the spiral wire 126 into the skin of the fetus 108 until the sensors 124 of the attachment end 122 are brought into contact with the fetus 108. The end of the wire harness 110 opposite the body 120 may be plugged into one of the ports 170 of the reference unit 104 to provide electrical power to the sensors 124 and/or for the sensors 124 to communicate sensor data to the reference unit 104.

The pressure catheter 106 may be inserted into the uterus of the mother and positioned such that the tube 150 is placed between the skin of the fetus and the uterine wall of the mother. The end of the wire harness 116 opposite the pressure catheter 106 may be plugged into the reference unit 104 to provide electrical power to the sensors of the pressure catheter and/or for the sensors to communicate sensor data to the reference unit 104. When desired, an amniotic flush may be provided via the port 152 of the pressure catheter 106. A medical professional may attach a syringe or other fluid source to the port 152 to force fluid through the valve and into the tube 150. The fluid travels within to the tube 150 to the end 154 where the fluid exits the tube 150 and flushes the uterus of the mother.

The reference unit 104 may be affixed to the patient. The sensors of the reference unit 104 may be positioned such that the reference electrodes and/or sensors contact or engage the skin of the mother to capture data from the mother for use in comparison with the data collected from the fetus. The reference unit 104 may be attached to the mother via a strap 114 that wraps around the leg or arm of the mother so that the sensors remain in contact with the skin of the mother. In another form, an adhesive is applied to the bottom 104A of the reference unit 104 and pressed against the skin of the mother to secure the reference unit 104 thereto. In one form, an adhesive has already been applied and a medical professional removes a paper or plastic backing to expose the adhesive of the bottom 104A of the reference unit 104 for attachment to the skin of the mother.

The reference unit 104 may process the sensor data received from the fetal sensor unit 102 and the pressure catheter 106 based on a comparison of the sensor data with the reference electrode data. In some forms, the reference unit 104 may communicate the processed sensor data to a display or to a remote computer for storage and/or additional processing. In forms where the reference unit 104 includes a display screen, the reference unit 104 may display the sensor data or diagnosed conditions of the fetus based on the sensor data collected from the fetal sensor unit 102, the pressure catheter 106, and the reference electrodes and/or sensors of the reference unit 104 via the display screen 172. The reference unit 104 may be attached such that the screen is oriented so that the mother may view the screen 172 with relative ease to monitor the sensor data.

Since the reference unit 104 is accessible, being affixed to the outer skin of the mother and not within the uterus of the mother, the sensors and reference electrodes of the reference unit 104 may be cleaned or sanitized. To clean or sanitize the sensors or reference electrodes of the reference unit 104, the reference unit 104 may be detached from the mother such that the reference electrodes and sensors no longer engage the skin of the mother. The sensors and reference electrodes may then be cleaned such as by wiping, scrubbing, and/or applying a cleaning agent to the sensors and/or reference electrodes. This cleaning process may be performed while the fetal sensor unit 102 remains attached to the fetus 108. Cleaning the sensors and/or reference electrodes of the reference unit 104 may increase the accuracy of the reading of the fetal monitoring system 100. The sensors and/or reference electrodes of the reference unit 104 may be cleaned regularly or may be cleaned when the output of the fetal monitoring system 100 appears to be inaccurate (e.g., the sensors have drifted).

Figure 6C:
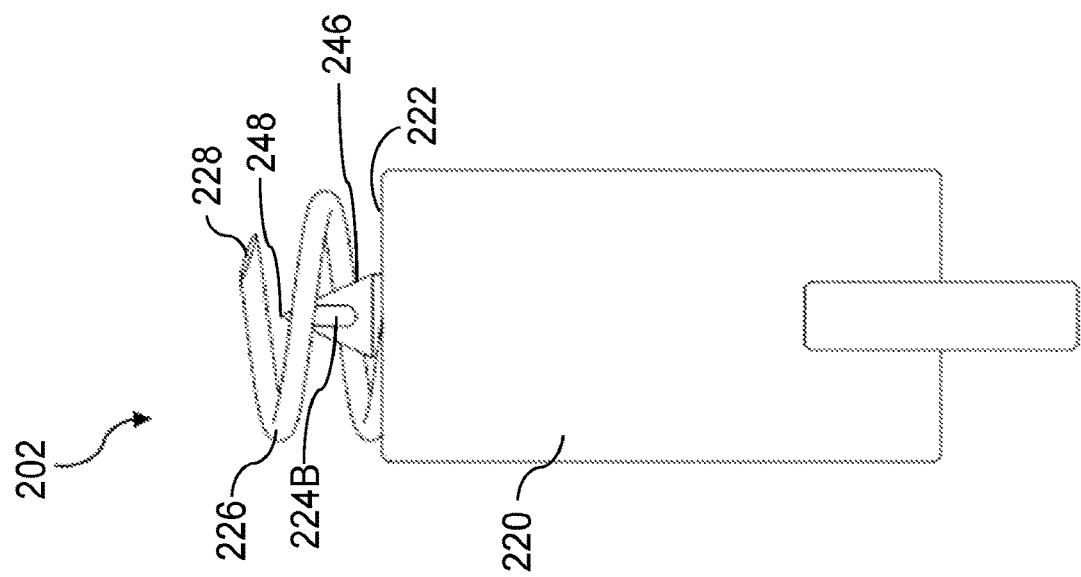
FIG. 6C is a right side elevation view of the fetal sensor unit of FIG. 6A.
Figure 6B:
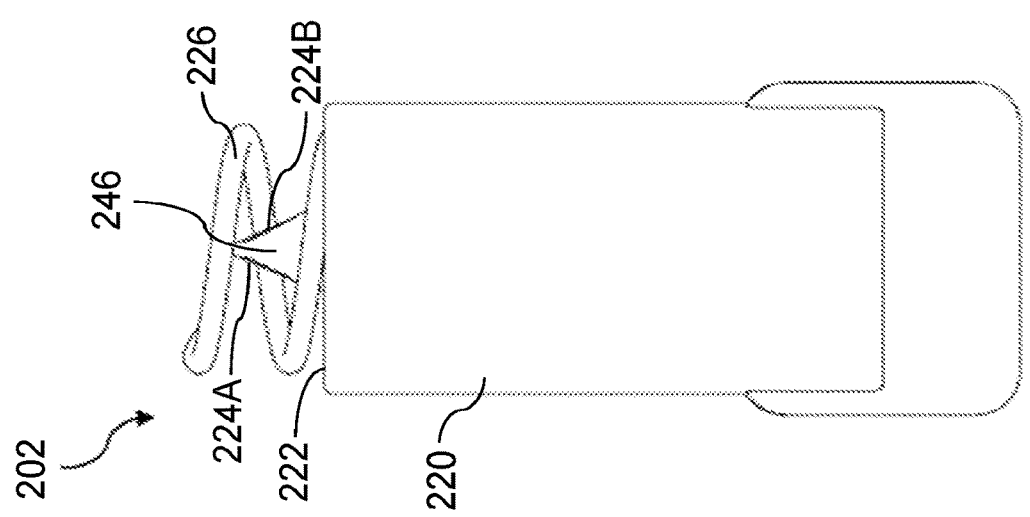
FIG. 6B is a front elevation view of the fetal sensor unit of FIG. 6A.
Figure 6A:
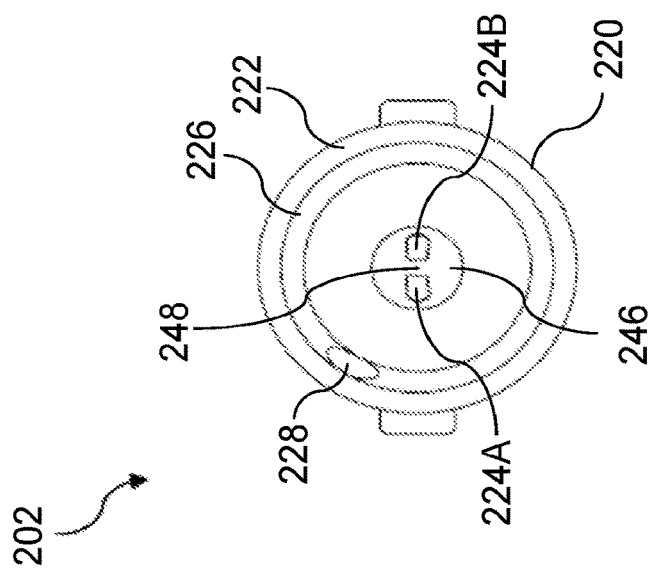
FIG. 6A is a top plan view of a fetal sensor unit according to a second embodiment.

With reference to FIGS. 6A-C, a fetal sensor unit 202 is shown according to a second embodiment. The fetal sensor unit 202 is similar to the fetal sensor unit 102 of the first embodiment, the primary differences of which are highlighted in the following discussion. The fetal sensor unit 202 of the second embodiment may be used in place of the fetal sensor unit 102. For conciseness and clarity, the references numeral used for features of the fetal sensor unit 102 of the first embodiment that correspond to similar features of the fetal sensor unit 202 of the second embodiment will be used with the prefix changed from a "1" to a "2." For example, a feature of the fetal sensor unit 102 referenced by the reference numeral "120" will be shown with reference numeral "220" with regard to the fetal sensor unit 202.

With reference to FIG. 6A-C, the fetal sensor unit 202 has a spiral wire 226 for attaching the fetal sensor unit 202 to a fetus 108. The fetal sensor unit 202 includes a probe 246 configured to piece the skin (e.g., the scalp of the fetus 108) extending from the attachment end 222 of the body 220. The probe 246 may be formed of a metal such as stainless steel, titanium or combinations of alloys. As shown in FIG. 6B, the probe 246 is substantially cone shaped with the tip 248 of the probe 246 extending away from the attachment end 222. When the fetal sensor unit 202 is attached to the fetus 108 via the spiral wire 226, the tip 248 of the probe 246 is brought into contact with the skin of the fetus 108 and pierces the skin. The probe 246 further provides a point about which the fetal sensor unit 202 may continue to be rotated without the fetal sensor unit 202 sliding along the skin of the fetus 108 as the fetal sensor unit 202 is being affixed to the fetus 108. The probe 246 thus aids to anchor the fetal sensor unit 202 at the point of attachment which prevents unnecessary damage to the surrounding skin. The probe 246 may include one or more sensors 224 disposed on an outer surface thereof proximal to the tip 248. These sensors 224 may be, as examples, a pH sensor for measuring the acidity of the blood, an ECG sensor for detecting the ECG and/or heart rate data of the fetus 108, a temperature sensor for measuring the temperature of the fetus 108, an pulse oximetry sensor for measuring the oxygen saturation levels of the blood or the fetus 108, and/or a bicarbonate sensor for measuring bicarbonate levels in the blood of the fetus 108. These sensors may operate similar to those described above in regard to the fetal sensor unit 102 of the first embodiment. In the embodiment shown, the probe 246 includes a pH sensor 224A and a bicarbonate sensor 224B disposed on opposite sides of the probe 246. Being proximal the tip 248 of the probe 246, when the tip 248 pierces the skin of the fetus, the sensors are brought into contact with the blood or other bodily fluid or tissue of the fetus. The sensors thus may collect data directly from the blood of the fetus. These sensors may operate similar to those described above in regard to the fetal sensor unit 102 of the first embodiment.

The fetal sensor unit 202 may further include a gasket about the periphery of the attachment end 222. When the fetal sensor unit 202 is affixed to the fetus 108, the gasket is brought into contact with the skin of the fetus and extend between the attachment end 222 and the fetus. The gasket encircles and/or encloses the portion of the skin of the fetus from which the sensors of the fetal sensor unit 202 collect data thereby forming a sensor chamber. The gasket may include hydrophobic layers which further aid to keep ambient fluids from entering the sensor chamber. The gasket thus aids to keeps exterior fluids and debris from entering the sensor chamber that may affect the sensor readings or otherwise inhibit the sensors from collecting accurate data from the fetus 108.

Figure 7B:
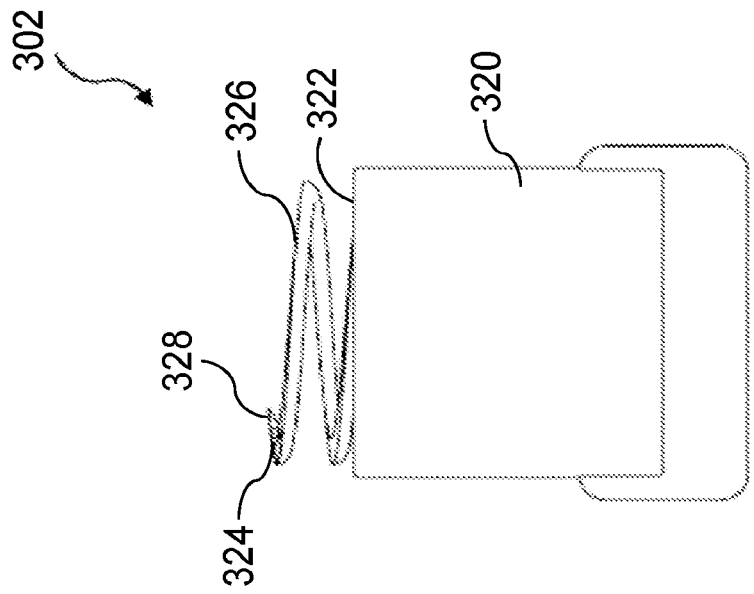
FIG. 7B is a front elevation view of the fetal sensor unit of FIG. 7A.
Figure 7A:
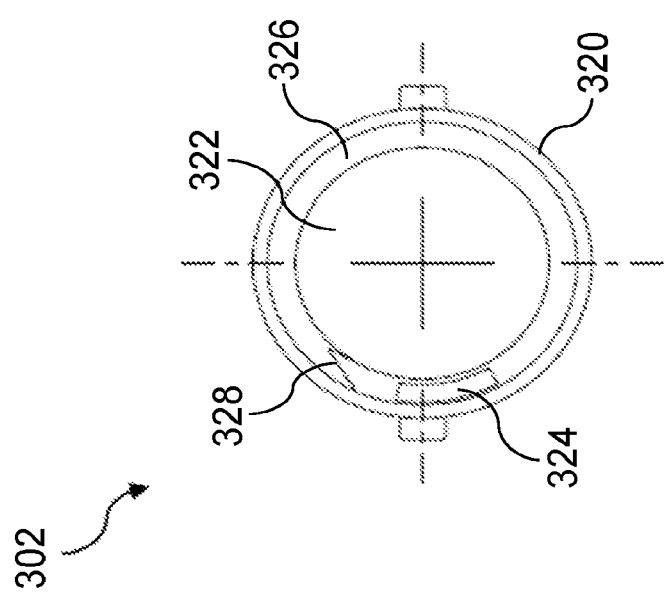
FIG. 7A is a top plan view of a fetal sensor unit according to a third embodiment.

With reference to FIGS. 7A-B, a fetal sensor unit 302 is shown according to a third embodiment. The fetal sensor unit 302 is similar to the fetal sensor units of the other embodiments previously described, the primary differences of which are highlighted in the following discussion. The fetal sensor unit 302 of the third embodiment may be used in place of the fetal sensor unit 102. For conciseness and clarity, the references numeral used for features of the fetal sensor unit 102 of the first embodiment that correspond to similar features of the fetal sensor unit 302 of the third embodiment will be used with the prefix changed from a "1" to a "3." For example, a feature of the fetal sensor unit 102 referenced by the reference numeral "120" will be shown with reference numeral "320" with regard to the fetal sensor unit 302.

With reference to FIG. 7A-B, the fetal sensor unit 302 shown does not include a central probe extending from the attachment end 322 as in the fetal sensor unit 202 of the second embodiment of FIGS. 6A-C. The fetal sensor unit 302 has a spiral wire 326 for attaching the fetal sensor unit 302 to a fetus 108 that is formed of a flat wire or a wire having a flat portion thereon rather than a round wire as shown in the previous embodiments. Additionally, the tip 328 of the spiral wire 326 includes a sensor 324 disposed thereon. In some forms, the spiral wire include multiple sensors 324 mounted thereto. These sensors 324 may be, as examples, a pH sensor for measuring the acidity of the blood, an ECG sensor for detecting the ECG and/or heart rate data of the fetus 108, a temperature sensor for measuring the temperature of the fetus 108, an pulse oximetry sensor for measuring the oxygen saturation levels of the blood or the fetus 108, and/or a bicarbonate sensor for measuring bicarbonate levels in the blood of the fetus 108. These sensors may operate similar to those described above in regard to the fetal sensor unit 102 of the first embodiment. Thus, when the fetal sensor unit 302 is affixed to the skin of the patient (e.g., the fetus) the one or more sensors 324 are passed into or underneath the outer surface of the skin of the patient. This enables the sensors 324 to be in direct fluid contact with the blood, bodily fluid, tissue, etc. of the patient.

Figure 8B:
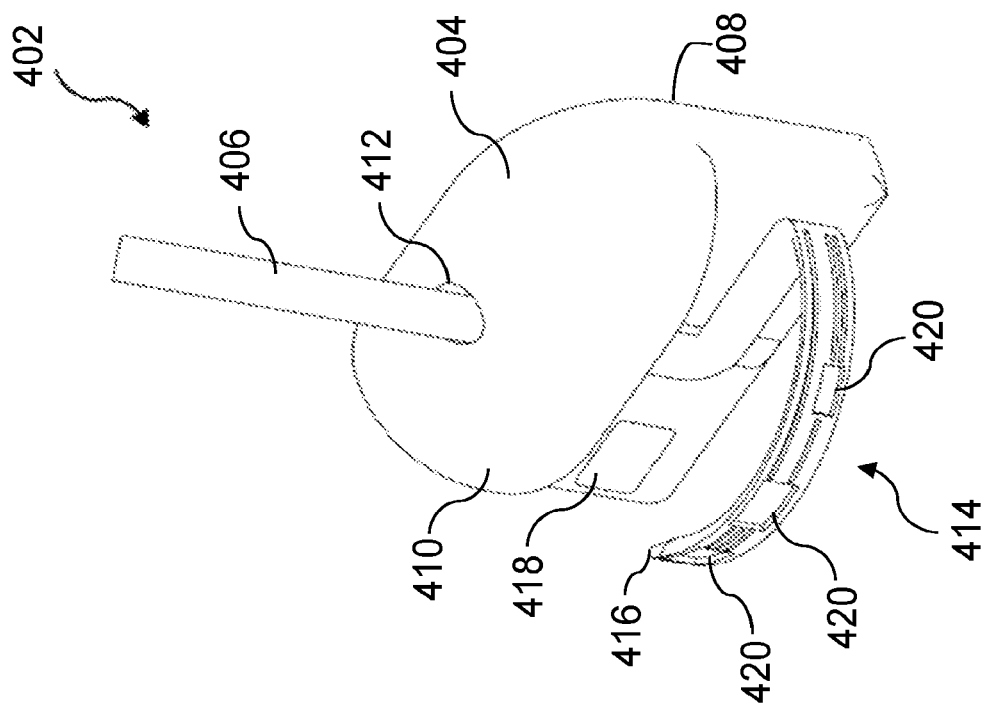
FIGS. 8A-B are bottom perspective views of a fetal sensor unit according to a fourth embodiment.
Figure 8A:
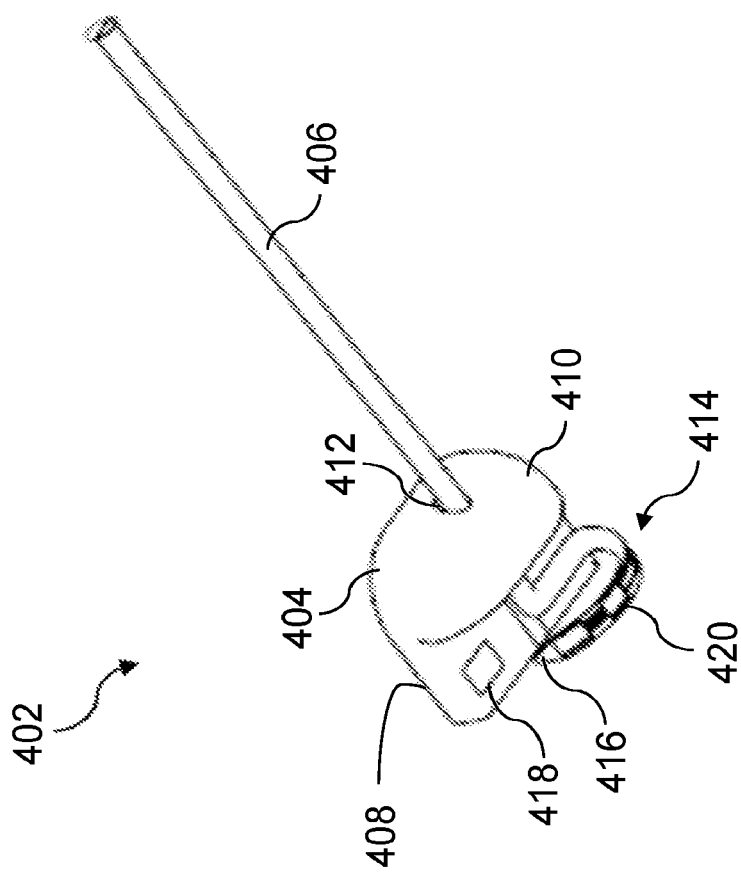
Figure 8C:
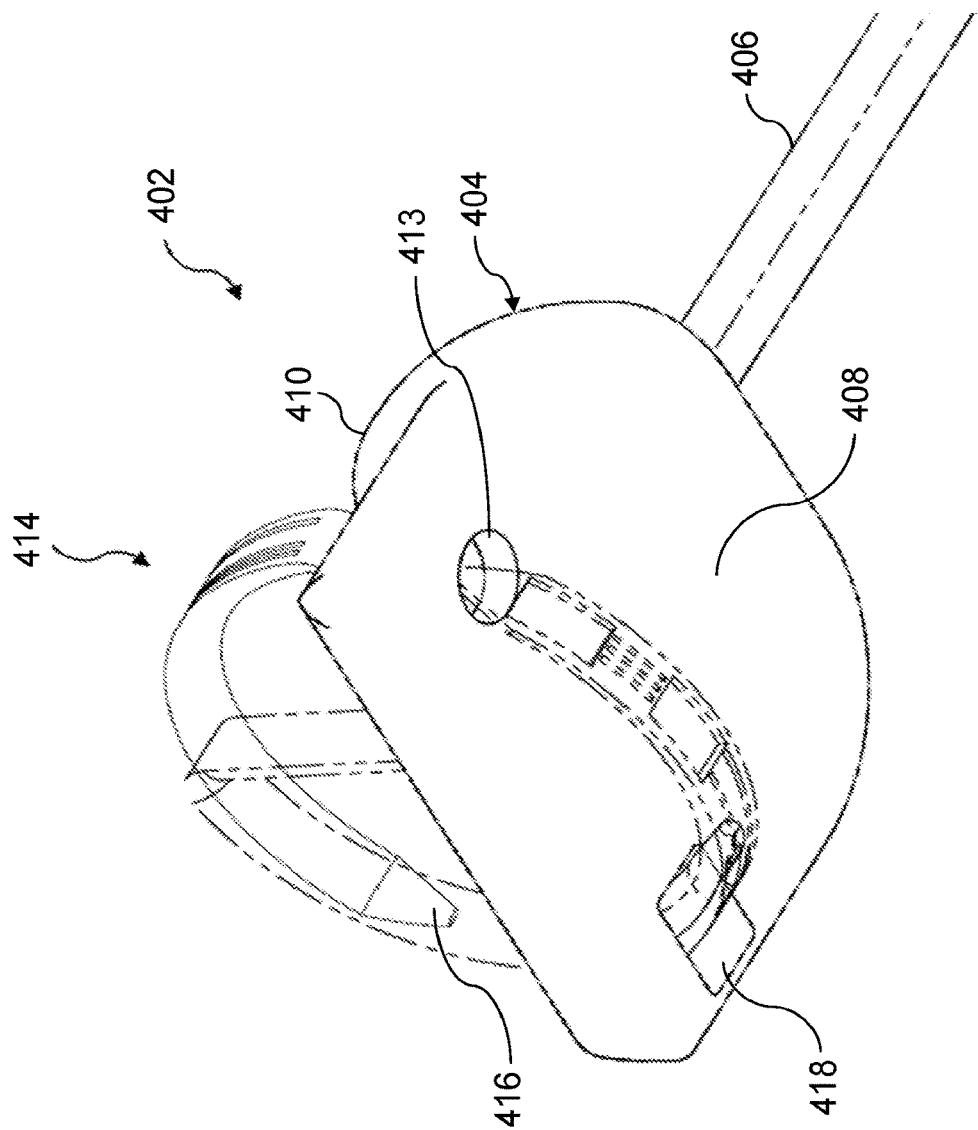
FIG. 8C is a top perspective view of the fetal sensor unit of FIG. 8A.

With reference to FIGS. 8A-C, a fetal sensor unit 402 is shown according a fourth embodiment. The fetal sensor unit 402 includes a body 404 and a rod or wire 406. The body 402 includes a flat surface 408 configured to engage the skin of a patient (e.g., fetus 108) and a protrusion 410 extending away from the flat surface 408. The protrusion 410 defines a hole 412 therethrough through which the wire 406 extends. The wire 406 may be formed of a plastic or a metal such as stainless steel, titanium, or an alloy. In the embodiment shown, the attachment end 414 is formed of a flat wire. In other embodiments, the attachment end 414 may be formed of a round wire. The end of the wire 406 includes an attachment end 414 where the wire is bent into a hook. The hook of the attachment end 414 terminates at a tip 416 that is configured to pierce skin. The tip 416 may terminate at a point or form a blade configured to pierce or cut into the skin.

With reference in particular to FIG. 8C, the wire 406 may be rotated relative to the body 404 about the axis formed by the hole 412 through the protrusion 410 of the body 404 through which the wire 406 extends. The body 404 further defines an insertion opening 418 extending through the flat portion 408 of the body 404. When the wire 406 is rotated, the tip 416 of the attachment end 414 may by passed through the insertion hole 412. As the wire 406 is continued to be rotated, the entire hook portion of the attachment end 414 may be passed through the insertion hole 412. The wire 406 may be rotated until the tip 416 is proximal to or in contact with a recess 413 on the flat surface 408 of the body 404 as indicated by the dashed line drawing of the attachment end 414. Thus, when the flat portion 408 is engaging the skin of a patient, rotation of the wire 406 in the direction to pass the tip 416 through the insertion hole 412 results in the tip 416 engaging and piercing the skin of the patient against which the flat portion 408 engages. Once the hook portion of the attachment end 414 is within the skin of the patient, the fetal sensor unit 402 is secured to the patient. In some forms, when the attachment end 414 is fully rotated to attach the fetal sensor unit 402 to the patient, the tip 416 pierces and exits the skin as the tip 416 is brough proximal to the flat surface 408. To detach the fetal sensor unit 402 from the patient, the wire 406 may be rotated in the opposite direction to withdraw the hook portion of the attachment end 414 from the skin of the patient and back through the insertion opening 418.

The fetal sensor unit 402 may include one or more sensors 420 mounted to the attachment end 414 of the wire 406. These sensors 420 may be, as examples, a pH sensor for measuring the acidity of the blood, an ECG sensor for detecting the ECG and/or heart rate data of the fetus 108, a temperature sensor for measuring the temperature of the fetus 108, an pulse oximetry sensor for measuring the oxygen saturation levels of the blood or the fetus 108, and/or a bicarbonate sensor for measuring bicarbonate levels in the blood of the fetus 108. These sensors may operate similar to those described above in regard to the fetal sensor unit 102 of the first embodiment. Being mounted to the attachment end 414 of the wire 406, when the wire 406 is rotated to attach the body 404 to the patient, the sensors 420 are inserted into the skin of the patient. Thus, when the fetal sensor unit 402 is secured to the patient, the sensors 420 are within or underneath the skin of the patient and in fluid contact or communication with the blood, bodily fluid, tissue, etc. of the patient. The sensors 420 may communicate the sensor data generated via the wire 406 (e.g., in embodiments where the wire is conductive) or a conductive pathway (e.g., a trace) or conductive wire extending along or within the wire 406. In other forms, the fetal sensor unit 402 may include one or more sensors 420 mounted on the flat portion 408 the body 404 that are brought into engagement with an outer surface of the skin when the fetal sensor unit is attached to the skin of the fetus.

Figure 9B:
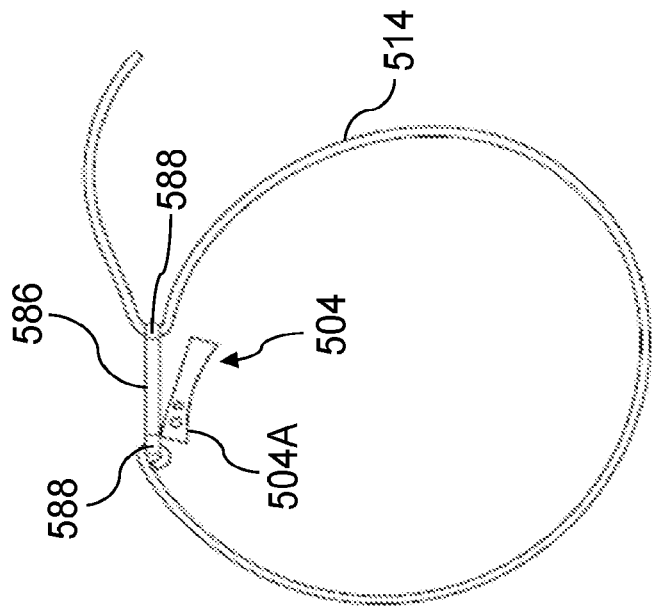
FIG. 9B is a left side elevation view of the reference unit of FIG. 9A.
Figure 9A:
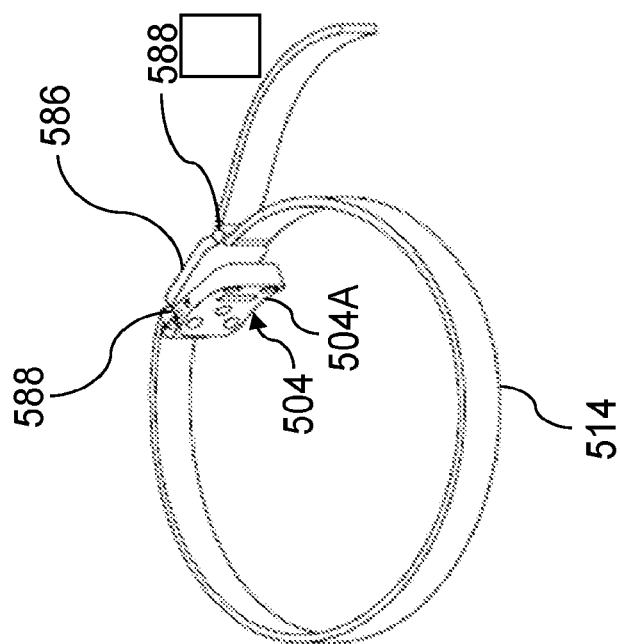
FIG. 9A. is a bottom perspective view of a reference unit according to a second embodiment.

With reference to FIG. 9A-B, a reference unit 504 according to a second embodiment is shown. The reference unit 504 is similar to the reference unit 104 of the first embodiment, the primary differences of which are highlighted in the following discussion. The reference unit 504 of the second embodiment may be used in place of the reference unit 104. For conciseness and clarity, the references numeral used for features of the reference unit 104 of the first embodiment that correspond to similar features of the reference unit 504 of the second embodiment will be used with the prefix changed from a "1" to a "5." For example, a feature of the reference unit 104 referenced by the reference numeral "114" will be shown with reference numeral "514" with regard to the reference unit 504.

The reference unit 504 does not include a display screen for displaying the sensor data of the fetal monitoring system 100. The reference unit 504 may include a display port that may be plugged into another display screen for displaying the sensor data or other conditions determined by the reference unit 504 (e.g., a diagnosis of fetal acidosis). In another form, the reference unit 504 includes communication circuitry for wirelessly communicating the sensor data collected by the reference unit 504 and/or the other sensors to the fetal monitoring system 100 to a remote computer or display. In some forms, the reference unit 504 may include a speaker, indicator lights, buzzer, or vibrator that is used to indicate when an abnormal or alarming condition is present as described in regard to the first embodiment.

Similar to the reference unit 104 of the first embodiment, the reference unit 504 includes a bottom surface 504A with a plurality of sensors and electrodes that is rounded and configured to engage the surface of the skin of the patient. As shown in FIGS. 9A-B, the reference unit 504 is hingedly connected to a bracket 586 including loops 588 through which a strap 514 extends. A first end of the strap 514 may be secured to a first loop 588. The second end of the strap 514 may pass through the second loop 588 such that the strap 514 forms a loop through which a portion of the patient's body (e.g., arm, leg, or abdomen) may extend when securing the reference unit 504 to the patient. The bottom surface 504A of the reference unit 504 faces the inside of the loop formed by the strap 514. Thus, once the portion of the patient's body (e.g., leg) is passed into the loop formed by the strap 514, the second end of the strap 514 may be drawn through the loop 588 to cinch the strap 514 about the patient to thereby cause the sensors on the bottom surface 504A of the reference unit 504 to engage the patient's skin and secure the reference unit 504 to the patient. The hinged connection between the reference unit 504 and the bracket 586 may bias the reference unit 504 away from the bracket 586 and against the patient's skin to ensure constant skin contact between the electrodes and the skin even when the strap 514 becomes loose.

Uses of singular terms such as "a," "an," are intended to cover both the singular and the plural, unless otherwise indicated herein or clearly contradicted by context. The terms "comprising," "having," "including," and "containing" are to be construed as open-ended terms. It is intended that the phrase "at least one of" as used herein be interpreted in the disjunctive sense. For example, the phrase "at least one of A and B" is intended to encompass only A, only B, or both A and B.

While there have been illustrated and described particular embodiments of the present invention, those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus for monitoring a physiological condition of a fetus in utero comprising:

a body having an attachment portion, the attachment portion configured to be inserted into skin of the fetus to affix the body to the fetus;

an ion-sensitive field-effect transistor (ISFET) sensor configured to generate sensor data corresponding to the physiological condition of the fetus and mounted to a portion of the attachment portion which is inserted into the skin of the fetus to affix the body to the fetus; and a reference sensor configured to generate reference data against the sensor data generated by the ISFET sensor, the reference sensor being positioned externally from the body and configured to engage an outer surface of a portion of the skin of the fetus.

2. The apparatus of claim 1 further comprising a processor communicatively coupled to the sensor and the reference sensor, the processor configured to receive the sensor data and the reference data and determine the physiological condition of the fetus based at least on part on the sensor data and the reference data.

3. The apparatus of claim 1 wherein the outer surface of the portion of the skin of the fetus engaged by the reference sensor is different from a portion of the skin of the fetus where the sensor is inserted thereto.

4. The apparatus of claim 1 wherein the reference sensor is held in engagement with the portion of the skin of the fetus via at least one of a strap, an adhesive, and a tape.

5. The apparatus of claim 1 wherein the attachment portion includes a segment of wire formed into a hook.

6. The apparatus of claim 5 wherein the attachment portion includes a helical wire.

7. The apparatus of claim 5 wherein the sensor is mounted proximal to a tip of the hook.

8. The apparatus of claim 5 wherein the hook is rotated to cause the hook to pierce the skin and insert a portion of the hook into the skin of the fetus to secure the body thereto.

9. The apparatus of claim 5 wherein the reference sensor is removable from engagement with the outer surface of the skin of the fetus while the sensor remains coupled to the fetus.

10. The apparatus of claim 1 further comprising a probe extending from a surface of the body and configured to pierce the skin of the fetus when the body is secured thereto by the attachment portion, the sensor mounted to a surface of the probe and configured to be brought into fluid communication with blood of the fetus when the body is secured to the fetus.

11. The apparatus of claim 10 further comprising a dispensing opening on the surface of the body, the dispensing opening in fluid communication with a channel extending through the body such that fluid forced through the channel exits the dispensing opening and flushes the skin of the fetus.

12. The apparatus of claim 1 wherein the attachment portion is a probe having a tip configured to pierce the skin of the fetus, the sensor mounted proximal the tip of the probe.

13. The apparatus of claim 10 wherein the probe is substantially cone shaped.

14. The apparatus of claim 1 wherein the fetus is in distress.

15. A fetal condition monitoring device comprising the apparatus of claim 1 and further comprising a display screen configured to display information based at least in part on the sensor data.

16. The fetal condition monitoring device of claim 15 further comprising a pressure catheter including a tube and one or more sensors coupled to the tube to determine contraction pressure and amniotic fluid analyte monitoring based on lactate or lactic acid.

17. The fetal condition monitoring device of claim 15 further comprising a dispensing opening in the body, the dispensing opening in fluid communication with a channel extending through the body such that fluid forced through the channel exits the dispensing opening and flushes the skin of the fetus.

18. The fetal condition monitoring device of claim 15 further comprising a probe extending from the body and configured to pierce the skin of the fetus when the body is affixed to the fetus by the attachment portion, the sensor mounted to a surface of the probe and configured to be brought into fluid communication with blood of the fetus when the body is affixed to the fetus.

19. The fetal condition monitoring device of claim 16 wherein the pressure catheter is connected to the reference sensor.

20. A method for monitoring a condition of a fetus comprising:

rotating an attachment portion of a sensor unit to secure the sensor unit to skin of the fetus and to bring a sensor of the sensor unit into engagement with the fetus, the sensor configured to generate sensor data pertaining to the condition of the fetus and communicate the sensor data to a processor;

engaging a reference sensor with an outer surface of a portion of the skin of the fetus, the reference sensor being configured to generate reference data against which the sensor data generated by the sensor is compared; and determining, by the processor, the condition of the fetus based at least in part on the sensor data and the reference data.

21. The method of claim 20 wherein the condition of the fetus is at least one of a blood pH level, blood bicarbonate level, blood oxygen saturation level, heart rate, and temperature.

22. The method of claim 20 wherein rotating the attachment portion to secure the sensor unit to the skin of the fetus brings the sensor into fluid communication with blood of the fetus.

23. The method of claim 20 wherein the fetus is in distress.

* * * * *